(12) United States Patent
McHale et al.

(10) Patent No.: US 12,042,286 B2
(45) Date of Patent: **\*Jul. 23, 2024**

(54) METHODS, DEVICES, SYSTEMS, AND KITS FOR AUTOMATED BLOOD COLLECTION BY FINGERSTICK

(71) Applicant: Labrador Diagnostics LLC, Wilmington, DE (US)

(72) Inventors: Patricia McHale, Palo Alto, CA (US); William Westrick, Palo Alto, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 983 days.

This patent is subject to a terminal disclaimer.

(21) Appl. No.: 16/934,547

(22) Filed: Jul. 21, 2020

(65) Prior Publication Data
US 2021/0038138 A1    Feb. 11, 2021

Related U.S. Application Data

(63) Continuation of application No. 15/087,109, filed on Mar. 31, 2016, now Pat. No. 10,722,163.

(60) Provisional application No. 62/141,184, filed on Mar. 31, 2015.

(51) Int. Cl.
| | |
|---|---|
| *A61B 5/15* | (2006.01) |
| *A61B 5/151* | (2006.01) |
| *G01N 33/49* | (2006.01) |
| *G01N 33/48* | (2006.01) |
| *G01N 33/487* | (2006.01) |

(52) U.S. Cl.
CPC .. *A61B 5/150068* (2013.01); *A61B 5/150022* (2013.01); *A61B 5/150076* (2013.01); *A61B 5/15186* (2013.01); *G01N 33/49* (2013.01); *A61B 5/15* (2013.01); *A61B 5/150053* (2013.01); *A61B 5/150061* (2013.01); *A61B 5/151* (2013.01); *G01N 33/48* (2013.01); *G01N 33/487* (2013.01)

(58) Field of Classification Search
CPC ........ A61B 5/150068; A61B 5/150022; A61B 5/150076; A61B 5/15186; A61B 5/155; A61B 5/157; A61B 5/15; A61B 5/150053; A61B 5/150061; A61B 5/151; G01N 33/49; G01N 33/48; G01N 33/487
See application file for complete search history.

(56) References Cited

U.S. PATENT DOCUMENTS

| | | | |
|---|---|---|---|
| 3,626,929 A | * 12/1971 | Sanz | A61B 5/150022 600/583 |
| 6,679,852 B1 | * 1/2004 | Schmelzeisen-Redeker | A61B 5/150389 600/583 |
| 2005/0215925 A1 | * 9/2005 | Chan | A61B 5/1411 600/583 |

(Continued)

*Primary Examiner* — Matthew Kremer
*Assistant Examiner* — Jonathan Drew Moroneso
(74) *Attorney, Agent, or Firm* — Sterne, Kessler, Goldstein & Fox P.L.L.C.

(57) ABSTRACT

Methods, devices, systems and kits for obtaining blood samples are provided. Devices include a cuff, a pressure source, and a timing mechanism. The methods include placing a cuff on a digit of a subject, inflating the cuff, and obtaining a small volume blood sample. The methods further include warming a digit lancing a digit pulsing the cuff; and providing a signal indicating the end of the sample collection time period.

19 Claims, 9 Drawing Sheets

(56) References Cited

U.S. PATENT DOCUMENTS

| | | | |
|---|---|---|---|
| 2009/0112125 A1* | 4/2009 | Tamir | A61B 5/150022 600/583 |
| 2010/0261988 A1* | 10/2010 | Tamir | A61B 5/150519 600/583 |
| 2017/0095622 A1* | 4/2017 | Bral | A61B 5/15105 |
| 2017/0325825 A1* | 11/2017 | Bybordi | A61B 5/150748 |

* cited by examiner

METHODS, DEVICES, SYSTEMS, AND KITS FOR AUTOMATED BLOOD COLLECTION BY FINGERSTICK

BACKGROUND

Many clinical diagnostic methods require a blood sample from a subject. Blood samples include, for example, venous blood samples, arterial blood samples, capillary blood samples, and mixed venous blood samples. Obtaining a blood sample typically requires puncturing the skin of a subject. For example, arterial and venous blood samples are typically obtained by inserting a needle or catheter into an artery or vein in order to obtain arterial or venous blood samples (respectively). Mixed venous blood samples may be obtained from the pulmonary artery (requiring an invasive procedure). Arterial and venous blood samples thus require puncturing the skin of a subject, in order to insert a portion of a needle or catheter into an artery or vein. Blood may be obtained without a needle, for example, by puncturing the skin of a subject and collecting blood that exits the puncture site. For example, a fingerstick blood sample may be obtained by lancing a digit (e.g., a finger) of a subject and collecting one or more drops of blood from the wound in the digit. Depending on the type and size of puncture, the amount of blood required, the time to obtain a blood sample, the quality of blood samples may be variable.

However, many subjects find giving blood samples to be unpleasant and painful. Moreover, different methods, different personnel (e.g., phlebotomists), and different subjects may provide different amounts and different qualities of blood when sampled. Thus, in addition to causing discomfort or pain to subjects, present methods of obtaining blood samples may be inconsistent, or may provide variable amounts of blood, or may provide blood samples of inadequate quality or integrity. Accordingly, improved methods of obtaining blood samples from subjects are desired.

INCORPORATION BY REFERENCE

All publications, patents, and patent applications mentioned in this specification are herein incorporated by reference to the same extent as if each individual publication, patent, or patent application was specifically and individually indicated to be incorporated by reference.

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2015 Theranos, Inc.

SUMMARY

Methods, devices, systems, and kits for obtaining blood samples from subjects are disclosed. In embodiments, devices, systems, methods, and kits disclosed herein are useful for collecting fingerstick blood samples from a digit (e.g., from a finger or toe). In embodiments, these devices, systems, methods, and kits provide automated pressure cycling for collection of blood during a fixed collection time period. In embodiments, such automated pressure cycling is provided by an inflatable cuff which fits around a digit. Such a cuff may be inflated and deflated repeatedly during at least part of the collection time period. In embodiments, these devices, systems, methods, and kits further provide digit warming as well as automated pressure cycling, and may further provide digit lancing as well as automated pressure cycling for collection of blood during a fixed collection time period. In embodiments, devices and systems as disclosed herein may include a pressure-interruption switch. In embodiments, devices, systems, and kits may include a sample collection element or device; a communication unit; a sample analysis element or device; and combinations thereof.

These methods, devices, systems and kits for obtaining blood samples may be used to easily and reliably obtain blood samples from subjects. These methods, devices, systems, and kits are designed so that no extensive amount of training or experience is required for their successful use in obtaining fingerstick samples from subjects. These methods, devices, systems, and kits provide advantages over previous methods, devices and systems by, for example, reliably providing improved blood flow for fingerstick blood sample collection, providing accurate timing of such sample collection, and greater ease of sample collection by a technician collecting a blood sample.

Small volume blood samples may be obtained from small punctures, incisions, or other wounds made in a digit of a subject (e.g., a finger or toe) or other skin surface of a subject (e.g., of a heel, of an earlobe, or of another location). Small volume blood samples may be obtained from a digit of a subject within a short period of time after the puncture, incision, or other wound is made. In embodiments, a short period of time is a time period which ends prior to the occurrence of significant coagulation of a blood sample collected from an incision or wound in a digit. In embodiments, a short period of time is a time period which ends prior to the occurrence of significant degradation of the integrity or of the quality of a blood sample collected from a puncture, an incision, or other wound in a digit. In embodiments, a short period of time is a period of time during which blood flowing from a puncture, incision, or other wound in a digit is primarily capillary blood, and such capillary blood is not significantly diluted by, or contaminated with, interstitial fluid. In embodiments, a short period of time is about 90 seconds or less, or is about 80 seconds or less, or is about 70 seconds or less, or is about 60 seconds or less. In embodiments, a short period of time is about 90 seconds. In embodiments, a short period of time is about 60 seconds.

Devices include a cuff configured to hold or encircle a digit and a pressure source configured to inflate the cuff. In embodiments, such a cuff is configured to compress or constrict at least a portion of a digit effective to reduce or curtail blood flow out of the digit. In embodiments, such a cuff is configured to repeatedly compress or constrict at least a portion of a digit (e.g., to repeatedly inflate and deflate a cuff placed around a digit) effective to reduce or curtail blood flow out of the digit. In embodiments, devices include a cuff, a pressure source, and a timing mechanism, wherein the cuff is operably connected to the pressure source, effective that the cuff may be inflated by the pressure source. A cuff may also be deflated following inflation. In embodiments, the timing mechanism and the pressure source are operably connected so that the application of pressure to the cuff may be regulated by the timing mechanism, effective that the cuff may be inflated for a desired period of time (termed a "pulse"); or may be inflated for a desired period of time and deflated for a desired period of time; or may be repeatedly inflated for a desired period of time and deflated for a desired period of time, providing a desired frequency of inflation (i.e., a series of pulses provided at a pulse frequency). Devices may further include one or more of a: warming mechanism, lancing mechanism; sample collection mechanisms, which may be or include an automated sample collection device; a sample analysis device, which may be or include an automated sample analysis device; and communication unit.

Thus, in embodiments, a device having features as disclosed herein may include a cuff configured to hold or encircle a digit, a pressure source, and a timing mechanism, wherein these elements are operably connected to inflate the cuff for a desired period of time, or to repeatedly inflate the cuff at a desired inflation frequency. In embodiments, a timing mechanism of a device having features as disclosed herein may provide a signal, or may control a signal device effective to provide a signal or multiple signals. In embodiments, such signals may alert a user to an event, or indicate that an operation or procedure (e.g., lancing a digit) is to be performed, or that an operation or procedure is to ended (e.g., end collecting a sample), or may indicate the beginning of a period of time, or may indicate the end of a period of time, or may signal other operation, event, or period of time. In embodiments, a device having features as disclosed herein may include a cuff configured to hold or encircle a digit, a pressure source, a timing mechanism, and a warming mechanism, wherein these elements are operably connected to warm the cuff (or to warm a digit within or in contact with the cuff), and to inflate the cuff for a desired period of time, or to repeatedly inflate the cuff at a desired inflation frequency. In embodiments, a device having features as disclosed herein may include a cuff configured to hold or encircle a digit, a pressure source, and a timing mechanism, wherein these elements are operably connected to inflate the cuff for a desired period of time, or to repeatedly inflate the cuff at a desired inflation frequency, the device also including a lancing mechanism configured to lance an exposed portion of a digit disposed within the cuff. In embodiments, a device having features as disclosed herein may include a cuff configured to hold or encircle a digit, a pressure source, a timing mechanism, and a warming mechanism, wherein these elements are operably connected to warm the cuff (or to warm a digit within or in contact with the cuff), and to inflate the cuff for a desired period of time, or to repeatedly inflate the cuff at a desired inflation frequency (where each inflation is followed by a deflation of the cuff), the device also including a lancing mechanism configured to lance an exposed portion of a digit disposed within the cuff. In embodiments, devices and systems disclosed herein may include a pressure-interruption switch configured to temporarily interrupt inflation, or to temporarily allow deflation, of the cuff.

Systems include such a device (e.g., a device having a cuff, a pressure source, and a timing mechanism; a device having a cuff, a pressure source, a timing mechanism, and a warming mechanism; a device having a cuff, a pressure source, a timing mechanism, and a lancing mechanism; or a device having a cuff, a pressure source, a timing mechanism, a warming mechanism, and a lancing mechanism), and may include sample collection, sample analysis, or communication devices.

Methods include placing a cuff on a digit of a subject, inflating the cuff, and obtaining a small volume blood sample. Methods may further include warming a digit; lancing a digit; pulsing the cuff; and providing a signal indicating the end of the sample collection time period. Methods may also include temporarily interrupting inflation of a cuff, for example, by activation of an interrupt switch to, e.g., temporarily stop inflation, or to temporarily block a conduit between the pressure source and the cuff, or to temporarily allow deflation of the cuff.

Kits may include a device, a sample collection vessel, and may include a disposable for use in sample collection.

Accordingly, Applicant discloses herein devices and systems including a cuff, a source of pressure, and a timing mechanism, and optionally other elements as discussed herein. Applicant discloses herein devices and systems including a cuff, a source of pressure, and a timing mechanism, and including a warming mechanism configured to warm a digit. Applicant discloses herein devices and systems including a cuff, a source of pressure, a timing mechanism, and including a lancing mechanism configured to puncture a digit effective to make a wound or incision providing blood for sample collection. Applicant discloses herein devices and systems including a cuff, a source of pressure, a timing mechanism, and a sample collection mechanism, the sample collection mechanism being configured to collect a small sample of blood from a puncture, incision, or other wound in a digit. Such devices may further include a lancing mechanism configured to puncture a digit effective to make a wound or incision providing blood for sample collection.

Applicant discloses herein devices and systems including a cuff, a source of pressure, a timing mechanism, and including an automated sample analysis device or an automated sample analysis system. Applicant discloses herein devices and systems including a cuff, a source of pressure, a timing mechanism, and including a communication unit effective to transmit data regarding a blood sample. Applicant discloses herein devices and systems including a cuff, a source of pressure, a timing mechanism, an automated sample analysis device or an automated sample analysis system, and including a communication unit effective to transmit data regarding a blood sample.

Applicant discloses herein devices and systems including a cuff, a source of pressure, a means to pulse the application of pressure, and a timing mechanism. As used herein, to pulse the application of pressure refers to periodic application of pressure, where periods of pressure application are separated by periods of release of pressure. For example, where pressure is applied to a digit by a cuff placed around the digit, a pulse of pressure is provided by inflation of the cuff, and repeated pulses are provided by repeated inflations of the cuff separated by (at least partial) deflations of the cuff. Repeated pulses of pressure (cycles of pressure), e.g., repeated pulses of inflation (cycles of inflation) may be provided at a desired frequency, where the frequency is determined by the time between inflations.

Applicant discloses herein devices and systems including a cuff, a source of pressure, a means to pulse the application of pressure, a timing mechanism, and including a warming mechanism configured to warm a digit. Applicant discloses herein devices and systems including a cuff, a source of pressure, a means to pulse the application of pressure, a timing mechanism, and further including a lancing mechanism configured to puncture a digit effective to make a wound or incision providing blood for sample collection, and optionally including a warming mechanism configured to warm a digit. Applicant discloses herein devices and systems including a cuff, a source of pressure, a means to pulse the application of pressure, a timing mechanism, and a sample collection mechanism for collecting a small sample of blood, and optionally including a warming mechanism configured to warm a digit. Applicant discloses herein devices and systems including a cuff, a source of pressure, a means to pulse the application of pressure, a timing mechanism, a lancing mechanism configured to puncture a digit effective to make a wound or incision providing blood for sample collection, a sample collection mechanism for collecting a small sample of blood, and optionally including a warming mechanism configured to warm a digit. A warming mechanism may be a variable warming mechanism, configured to provide greater or lesser amounts of warming, i.e., may be configured to warm a digit to different temperatures. A variable warming mechanism may be configured to warm a digit to a desired temperature. For example, a variable warming mechanism may be configured to warm a digit to about 2° C. above normal skin temperature, or to about 3° C. above normal skin temperature, or to about 4° C. above normal skin temperature, or to about 5° C. above normal skin temperature, or higher Applicant discloses herein devices and systems including a cuff, a source of pressure, a timing mechanism, and including an automated sample analysis device or an automated sample analysis system. Applicant discloses herein devices and systems including a cuff, a source of pressure, a timing mechanism, and including a communication unit effective to transmit data regarding a blood sample. Applicant discloses herein devices and systems including a cuff, a source of pressure, a timing mechanism, an automated sample analysis device or an automated sample analysis system and including a communication unit effective to transmit data regarding a blood sample.

The methods, devices, and systems disclosed herein may be used to obtain blood samples from subjects. Blood samples may be obtained from a digit of a subject, e.g., from a finger or a toe of a subject, or other skin surface. The methods, devices, and systems disclosed herein may be used to obtain blood samples for clinical use, including, for example, for screening, monitoring, diagnostic, research, and other uses.

In embodiments, the devices, systems, methods, and kits are configured to aid in the collection of blood from puncture, incision, or other wound in a digit or other skin surface of a subject. In embodiments, aiding the collection of blood from a puncture, incision or other wound includes increasing the flow of blood from the wound for sample collection (as compared to the flow that would otherwise occur). In embodiments, such collection of blood is aided by inflation of a cuff effective to compress or constrict at least a portion of a digit and so to reduce or curtail blood flow out of the digit.

In embodiments, the devices and systems disclosed herein are configured to apply pressure to a digit to aid in collecting blood from a puncture or incision in that digit. In embodiments, the devices and systems disclosed herein are configured to apply pressure pulses to a digit to aid in collecting blood from a puncture or incision in that digit. In embodiments, the devices and systems disclosed herein are configured to apply pressure pulses for a period of time to a digit to aid in collecting blood from a puncture or incision in that digit. In embodiments, the period of time is determined by a timing mechanism; in embodiments, such a timing mechanism is included in the devices and systems disclosed herein. In embodiments, the devices and systems disclosed herein are configured to apply pressure pulses to a digit to aid in collecting blood from a puncture or incision in that digit, where such pressure pulses are applied at a desired frequency. In embodiments, the devices and systems disclosed herein are configured to apply pressure pulses to a digit to aid in collecting blood from a puncture or incision in that digit, where such pressure pulses are separated by one or more periods of lesser pressure, or of no pressure. In embodiments, the devices and systems disclosed herein are configured to apply pressure pulses to a digit to aid in collecting blood from a puncture or incision in that digit, where such pressure pulses are provided at a desired frequency and such pulses are separated by one or more periods of lesser pressure, or of no pressure. Such periods of applied pressure may be set to be of a desired duration, and such periods of lesser or no pressure may be set to be of a desired duration.

In embodiments, the devices and systems disclosed herein are configured to apply pressure to a digit to aid in collecting blood from a puncture or incision in that digit, and to warm at least a portion of that digit. In embodiments, such warming precedes collection of blood from that digit. In embodiments, the devices and systems disclosed herein are configured to apply pressure to a digit to aid in collecting blood from a puncture or incision in that digit, and include an element configured to puncture, or to otherwise wound, a digit of a subject effective to provide a passage for the flow of that subject's blood out of that digit.

In embodiments of the methods disclosed herein, a digit of a subject is compressed by a cuff of a device or system disclosed herein, and is then punctured, or otherwise wounded, effective to provide a passage for the flow of that subject's blood out of that digit. In embodiments of the methods disclosed herein, a digit of a subject is warmed and is compressed by a cuff of a device or system disclosed herein, and is then punctured, or otherwise wounded, effective to provide a passage for the flow of that subject's blood out of that digit. In embodiments of such methods, such warming precedes lancing of the digit, and precedes collection of blood from that digit. In embodiments, a digit is warmed for at least about 30 seconds, or at least about 45 seconds, or at least about 60 seconds prior to lancing of the digit. Warming of a digit may be provided by a cuff applied to the digit; in embodiments, warming precedes inflation of the cuff. In embodiments, warming may be provided while the cuff is inflated. In embodiments, warming may be provided prior to inflation of the cuff, and also while the cuff is inflated.

In embodiments of such methods disclosed herein, wherein a digit of a subject is compressed by a cuff of a device or system disclosed herein, such compression may comprise application of pressure for a period of time to a digit to aid in collecting blood from a puncture or incision in that digit. In embodiments, the period of time may be determined by a timing mechanism; in embodiments, the period of time may be determined by an operator of the device or system. In embodiments, the period of time is a short period of time. In embodiments, the period of time may be a period of time which ends prior to the occurrence of significant coagulation of a blood sample collected from an incision or wound in a digit. In embodiments, the period of time is a period which ends prior to the occurrence of significant degradation of the integrity or of the quality of a blood sample collected from an incision or wound in a digit. In embodiments, the period of time is a period which ends prior to significant mixing of interstitial fluid with blood in a sample collected from an incision or wound in a digit.

In embodiments of such methods disclosed herein, wherein a digit of a subject is compressed by a cuff of a device or system disclosed herein, such compression may comprise pulses of pressure applied to that digit. In embodiments of such methods disclosed herein comprising pulses of pressure, such pressure pulses may be applied at a desired frequency. In embodiments, such pressure pulses may be separated by one or more periods of lesser pressure, or of no pressure. In embodiments, such pressure pulses may be provided at a desired frequency and such pulses are separated by one or more periods of lesser pressure, or of no pressure, where such periods are of a desired duration.

In embodiments of the methods disclosed herein, a digit of a subject may be punctured, or otherwise wounded, by manual lancing effective to provide a passage for the flow of that subject's blood out of that digit. In embodiments of the methods disclosed herein, a digit of a subject is compressed by a cuff of a device or system disclosed herein, and is then punctured, or otherwise wounded, by manual lancing effective to provide a passage for the flow of that subject's blood out of that digit. In embodiments of the methods disclosed herein, a digit of a subject is warmed and is compressed by a cuff of a device or system disclosed herein, and is then punctured, or otherwise wounded, by manual lancing effective to provide a passage for the flow of that subject's blood out of that digit.

In embodiments of the methods disclosed herein, a digit of a subject may be punctured, or otherwise wounded, effective to provide a passage for the flow of that subject's blood out of that digit, by a device or system disclosed herein. In embodiments of the methods disclosed herein, a digit of a subject is compressed by a cuff of a device or system disclosed herein, and is then punctured, or otherwise wounded, by a device or system disclosed herein effective to provide a passage for the flow of that subject's blood out of that digit. In embodiments of the methods disclosed herein, a digit of a subject is warmed and is compressed by a cuff of a device or system disclosed herein, and is then punctured, or otherwise wounded, by a device or system disclosed herein effective to provide a passage for the flow of that subject's blood out of that digit.

Applicant further provides a kit for fingerstick blood collection, comprising a device as disclosed herein and a sample collection vessel. In an embodiment, a kit for fingerstick blood collection comprises a device as disclosed herein, a sample collection vessel, and a disposable for use in sample collection. In embodiments, a disposable for use in sample collection may be a sterile swab (e.g., an alcohol swab), may be an absorbent pad (e.g., a cotton gauze pad for placement over a fingerstick wound), may be a bandage (e.g., a small self-adhesive bandage for placement over a fingerstick wound or over a gauze pad on a fingerstick wound), other disposables for use in a sample collection location (e.g., a clinical laboratory, a doctor's office, a clinic, a retail location, or other location in which a fingerstick sample may be obtained from a subject), and combinations thereof. In embodiments, a sample may be collected at a point-of-care location, such as a point-of-care location selected from the group of point-of-care locations consisting of a hospital, a doctor's office, a clinic, and combinations thereof On occasion, according to prior methods, a finger of a subject may have been manually squeezed by a technician prior to, or during, collection of a fingerstick blood sample. However, the amount and duration of squeezing may have varied depending on the phlebotomist obtaining the fingerstick sample and the subject from whom it is obtained, thus leading to undesirable variation in the amount and quality of blood obtained from a fingerstick.

The devices, systems, and methods disclosed herein provide advantages over prior methods by automating some or all steps required for the collection of fingerstick blood samples from a subject. In prior methods, a technician gripped a digit and applied pressure to the digit manually. In embodiments, the devices, systems, and methods disclosed herein provide automation of some or all steps required for the collection of fingerstick blood samples from a subject. Thus, the devices, systems, and methods disclosed herein provide an advantage by eliminating the dependency on technician grip technique by applying pressure to a digit by inflating a cuff placed around the digit. Thus, the devices, systems, and methods disclosed herein comprising an inflatable cuff improve methods for obtaining small blood samples by minimizing the amount of technician training that is required to train a technician to extract a quality blood sample from a fingerstick. The devices, systems, and methods disclosed herein provide advantages by providing control of the total time allowed for fingerstick blood collection. The devices, systems, and methods disclosed herein provide advantages by improving standardization and consistency of the fingerstick blood collection process. The devices, systems, and methods disclosed herein provide advantages by providing a signal indicating the beginning of a time period for blood collection. The devices, systems, and methods disclosed herein provide advantages by providing a signal indicating the end of an optimal time period for blood collection. The devices, systems, and methods disclosed herein provide advantages by preventing blood collection at times outside of the optimal time period for fingerstick blood collection. By automating some or all steps of the fingerstick blood collection process, the devices, systems, and methods disclosed herein provide advantages by reducing or eliminating the potential for repetitive motion injury of the phlebotomists' hands.

Applicant discloses herein methods, devices, systems, and kits for automated fingerstick blood collection. These methods, devices, systems, and kits are simple and straightforward to use. These methods, devices, systems, and kits are designed so that no extensive amount of training or experience is required for their successful use in obtaining fingerstick samples from subjects. Thus, the methods, devices, systems, and kits disclosed herein are designed for use by both sophisticated and unsophisticated technicians and phlebotomists, and offer advantages including ease of use and wide applicability. The advantages provided by the methods, devices and systems disclosed herein include, for example, improved blood flow for fingerstick blood sample collection, more accurate timing of such sample collection, greater control over the quality of the blood sample collected by avoidance of over-long collection periods (which may result in excessive contamination of the blood sample by interstitial fluid), and greater ease of sample collection by a technician. The advantages provided by the methods, devices and systems disclosed herein further include, for example, greater control and greater consistency of sample collection, and reduced risk of unsuccessful sample collection.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
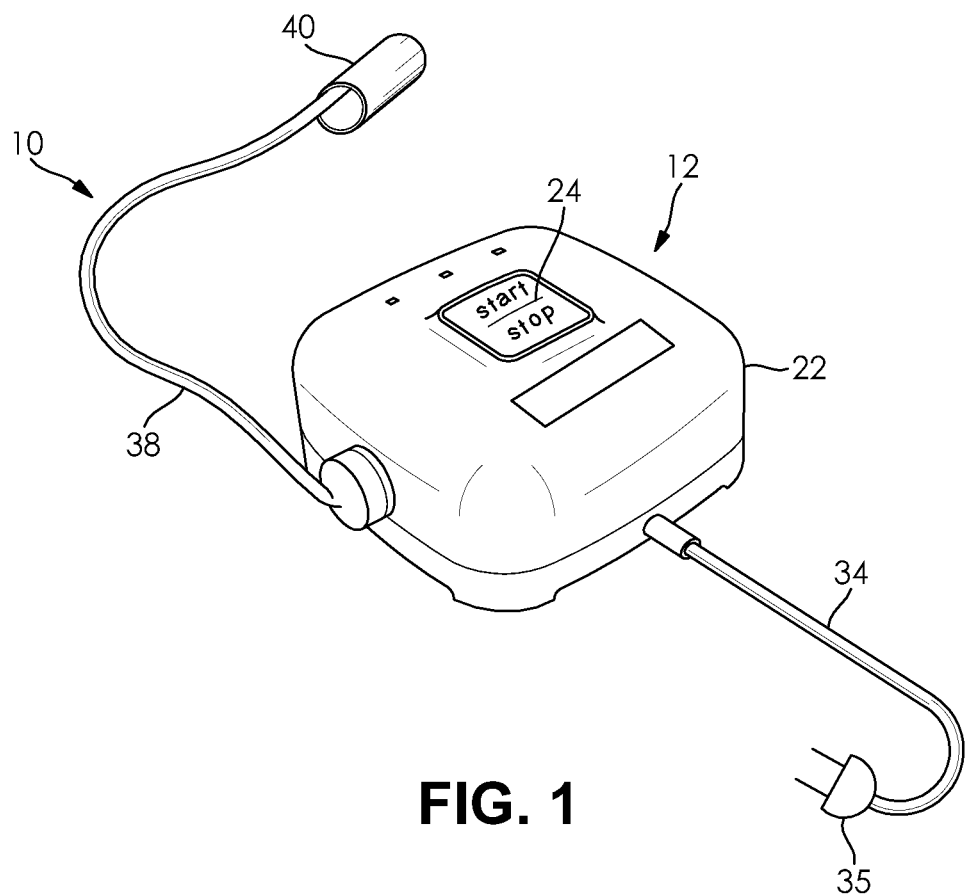
FIG. 1 shows an exemplary device having features as disclosed herein, including a pressure cuff attached to a control unit, the control unit including a pump effective to apply pressure to the cuff under the control of the control unit, and a power cable for connecting to a power source (e.g., an electrical cable with plug for connecting to an electrical power outlet).

Description and disclosure of examples of methods, devices, and systems which may use, or be used with, method, devices, and systems disclosed herein may be found, for example, in U.S. Patent Application 61/874,893, filed Sep. 6, 2013; U.S. Patent Application 61/803,449, filed Mar. 19, 2013; U.S. patent application Ser. No. 14/220,013, filed Mar. 19, 2014; in U.S. patent application Ser. No. 14/183,503, filed Feb. 18, 2014; in U.S. Pat. No. 8,840,838, filed Sep. 26, 2011; in U.S. Pat. No. 8,475,739, filed Sep. 26, 2011; and in U.S. Pat. No. 8,435,738, filed Sep. 26, 2011, the disclosures of which patents and patent applications are all hereby incorporated by reference in their entireties.

Definitions

Before the present methods, devices, and systems are disclosed and described, it is to be understood that the terminology used herein is for the purpose of describing particular embodiments only and is not intended to be limiting. It is also to be understood that the present disclosure provides explanatory and exemplary descriptions and examples, so that, unless otherwise indicated, the devices, systems, and methods disclosed herein are not limited to the specific embodiments described herein. Accordingly, in this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

Methods, devices, systems, and kits for collecting blood from a digit are disclosed herein. In embodiments, blood may be obtained from a digit by creating a puncture wound or incision through the skin of the digit, effective to allow blood to flow out of the digit for collection. Such puncturing or incising of the skin of a digit may be termed a "fingerstick". Blood obtained by fingerstick from a digit may be termed "fingerstick blood" or a "fingerstick blood sample" or a "fingerstick sample". As used herein, a digit may be a finger, or a toe, a heel, an ear (e.g., an earlobe), or other body portion.

It will be understood that methods, devices, systems, and kits disclosed herein may be used to obtain fingerstick blood samples from a digit, e.g., from a finger or from a toe of a subject, and in addition may be used to obtain small volume blood samples from, e.g., a heel or other surface of a subject. In embodiments, such small volume blood samples obtained from, e.g., a heel or other surface of a subject may be obtained from an infant subject, or a young child, or from an adult subject suffering from injuries or from a condition which prevents or makes difficult obtaining a blood sample from a finger or from a toe.

For example, a subject's finger (or toe, or heel, or other portion of the subject's body) may be punctured to yield a blood sample. Lancing may be manually performed, or may be automatically performed. The blood sample may be collected using a capillary tube, pipette, swab, drop, or any other mechanism known in the art. Blood collection may be manually performed, or may be automatically performed.

A blood sample may be drawn from a subject and provided to a device in a variety of ways, including but not limited to, by fingerstick. Blood may be liberated from the skin of a subject by lancing with a lancet, needle, or other blade or sharp implement. A sample collector may include a capillary, tube, pipette, syringe, venous draw, or any other collector. In one embodiment, a lancet punctures the skin and a sample may be drawn from the wound using, for example, gravity, capillary action, aspiration, or vacuum force. A sample collection device will typically not include a lancet. A sample collection device may be disposable. In embodiments, a sample collection device may include a lancet, which may be disposable. In embodiments, a sample collection device including a lancet may be disposable.

In embodiments, a subject's finger (or other portion of the subject's body) may be punctured (i.e., lanced) to yield a blood sample. Puncture (lancing) of a digit may be performed manually. In embodiments, lancing may be performed automatically. In embodiments, a lancet may be activated by a variety of mechanical, electrical, electromechanical, or any other known activation mechanism or any combination of such methods. Examples of other portions of the subject's body from which a blood sample may be collected include, but are not limited to, the subject's hand, wrist, arm, torso, leg, foot, ear, or neck. The blood sample may be collected using a capillary tube, pipette, or any other mechanism known in the art. The capillary tube or pipette may be a separate device, or may be a part of a device, cartridge, or vessel. The collected sample may be placed within a sample analysis device or system.

As used herein, a "finger-stick" refers to: i) the act of making a small puncture or incision in the skin of a subject, allowing a small amount (e.g., a drop, or one, two, or a few drops) of blood to flow and become available for collection; ii) the puncture itself; and iii) the blood collected thereby. Blood may be liberated in a finger-stick, for example, by use of a lancet or other sharp implement effective to pierce the skin of a subject. Typically, only a small amount of blood is collected in this way.

A blood sample obtained from a fingerstick is termed herein a "fingerstick sample". In embodiments, a fingerstick sample is obtained from a puncture or incision made in a digit, such as a finger, or a toe, of the subject. In embodiments, a fingerstick sample is obtained from a puncture or incision made in any suitable skin surface of a subject, such as, e.g., an ear (e.g., an earlobe), a heel, or other portion of a subject.

In embodiments, a digit may be a finger or toe. In embodiments of fingerstick samples obtained from a digit, a puncture, incision, or other wound may be made in a finger tip, or in a tip of a toe, of the subject. In embodiments, a fingerstick blood sample may be obtained from a heel of a subject, or from an earlobe, or other portion of an ear, or other portion of the body of a subject.

The term "fingerstick blood collection" as used herein refers to collection of small volume blood samples from a subject, typically following use of a lancet to produce a small wound in the skin of a subject. It will be understood that blood may be collected by "fingerstick blood collection" from any portion of a subject's body, and not only from a finger. For example, in embodiments, blood may be collected from a toe of a subject by "fingerstick blood collection". In embodiments, blood may be collected from a heel of a subject by "fingerstick blood collection". In embodiments, blood may be collected from an ear (e.g., from an earlobe) of a subject by "fingerstick blood collection". In embodiments, blood may be collected from any body surface of a subject by "fingerstick blood collection".

When referring to a volume, e.g., a "finger-stick volume" or "the volume of a finger-stick", the term "finger-stick" refers to the volume of a few drops of blood typically obtained from a finger-stick. A single drop of blood may have a volume of about 20-50 e.g., about 40 µL. Thus, a few drops of blood obtained from a finger-stick may provide a volume of about 50 µL to about 250 or about 75 µL to about 200 or, in some instances, between about 100-150 µL. Advantages of obtaining blood from a finger-stick include minimal discomfort to the subject and ease of access, as compared to obtaining blood from a vein or artery. Typically, only a small amount of blood is collected in this way. In embodiments, a fingerstick blood sample may be a blood sample having a volume of about 300 µL; or about 250 µL; or about 200 µL; or about 175 µL; or about 150 µL; or about 125 µL; or about 100 µL; or about 75 µL; or about 50 µL; or about 45 µL; or about 40 µL; or about 35 µL; or about 30 µL; or about 25 µL; or about 20 µL; or about 15 µL; or about 10 µL; or about 5 µL; or other small volume. Blood from a finger-stick may be collected, e.g., by needle, syringe, capillary tube, sample collection vessel, or by other implement or method. Blood from a finger-stick may be collected for transport to another location; for storage prior to use or analysis; for immediate use; or for a combination of the same.

As used herein, a "sample" may be a fingerstick blood sample, or may be any small volume blood sample, or may be any blood sample, or a portion of a blood sample. A sample may be of any suitable size or volume, and is preferably of small size or volume. A blood sample may be obtained from a digit (i.e., a finger or a toe); from a heel; from an earlobe; or from any other skin surface of a patient. A "fingerstick blood sample" collected from an infant, for example, will typically be collected by lancing a heel of the infant (and such lancing will typically be made with a shorter lancet, to produce a shallower wound, than would be the case for an adult subject).

In embodiments of the assays and methods disclosed herein, measurements may be made using a small volume blood sample, or no more than a small volume portion of a blood sample, where a small volume comprises no more than about 300 µL; or no more than about 250 µL; or no more than about 200 µL; or no more than about 150 µL; or no more than about 100 µL; or no more than about 75 µL; or no more than about 50 µL; or no more than about 35 µL; or no more than about 25 µL; or no more than about 20 µL; or no more than about 15 µL; or no more than about 10 µL; or no more than about 5 µL; or no more than about 3 µL; or no more than about 2 µL; or no more than about 1 µL; or no more than about 0.5 µL.

The term "lancing" as used herein refers to the act of making a small opening in the skin of a subject; such an opening may be a puncture, or an incision, or other wound which allows blood to flow out of the wound and onto the skin of the subject, providing a sample of blood may be that may be collected, e.g., for analysis. A wound made by lancing may be made by a lancet, which may be a needle, a blade, a plurality of needles, blades, and combinations thereof. As used herein, a puncture, incision, or other wound is typically a shallow wound, e.g., about 1 or 2 millimeters (mm) or less in depth measured form the skin surface (for an adult subject; such a wound for obtaining a blood sample from an infant may be about 0.5 to about 1 mm in depth, or less).

The term "lancet" as used herein refers to a needle, blade, or other sharp implement used to make a small wound in the skin for obtaining a blood sample, such as a fingerstick blood sample, which is typically a sample of capillary blood. A lancet suitable for use on the digit of an adult patient may make a wound of about 1 to 2 millimeters (mm) in depth, and may make a wound of less than about 1 mm in depth for an infant. The total length of a lancet suitable for making wounds of such depths will typically be longer than these depths, e.g., a lancet for making a wound of about 1 to 2 mm in depth may be about 3 to about 5 mm long, or longer. The depth of penetration may be limited during lancing by control of the insertion mechanism, by inclusion of a stop or guard on the lancet or on a mechanism holding or otherwise controlling the motion of the lancet, or by other means.

As used herein, a puncture, incision, or other wound is typically a shallow wound, e.g., about 1 or 2 millimeters (mm) or less in depth measured from the skin surface.

As used herein, the term "cuff" refers to an inflatable structure having a partially, or completely, tubular configuration, which may be placed on or around a digit (such as a finger or a toe) with the digit disposed within the interior portion of the tubular structure. Where the cuff forms a completely tubular structure, the digit fits within the cuff, with the cuff placed somewhat like a ring around the digit; typically, when in place, a cuff leaves a distal portion of the digit uncovered even when inflated. Where the cuff forms a partially tubular structure, the digit fits within the cuff, with the cuff placed around the digit somewhat like a ring which has a gap; typically, when in place, such a cuff also leaves a distal portion of the digit uncovered even when inflated.

As used herein, the phrases "internal diameter" and "cuff internal diameter" refer to the distance between one side of the interior wall of a deflated cuff to the other side of the interior wall of the deflated cuff. The internal diameter is measured along a diameter (for cuffs of substantially circular cross-section) or along a line that crosses a center or crosses between centers (for cuffs having substantially elliptical or oval cross-sections). An internal diameter may be measured for cuffs which are configured to completely encircle a digit (i.e., cuffs which have cross-sections that form closed loops) and may be measured for cuffs which are configured to partially encircle a digit (i.e., cuffs which have cross-sections that do not form closed loops; in such a case, the internal diameter may be measured from one inner wall to the opposite inner wall across a center, or centers, of a closed curve which lies substantially along the open cross-sectional curve of the cuff interior surface).

Applicant uses the term "pulse" to refer to application of pressure to a digit, constriction of a digit, or compression of a digit. A "pulse" and a "pressure pulse" may be provided by a cuff. Inflation of a cuff, followed by deflation (or decrease in the amount of inflation) provides a pulse. Multiple pulses may be provided during cyclic inflations (where the inflations may be separated by periods of deflation); the rate of providing such inflations (e.g., once per second, or once per two seconds, or other rate) is termed the "pulse frequency." A pulse frequency may be, for example, at least about 15 cycles per minute, or at least about 20 cycles per minute, or at least about 30 cycles per minute. In embodiments of pulses, the duration of inflation of a cuff is substantially equal to the duration of deflation of the cuff. For example, in embodiments of pulses, the duration of cuff inflation may be about 1 second, and the duration of cuff deflation may be about 1 second. In embodiments of pulses, the duration of cuff inflation may be about 2 seconds, and the duration of cuff deflation may be about 2 seconds. In embodiments of pulses, the duration of inflation of a cuff is different than the duration of deflation of the cuff. For example, in embodiments of pulses, the duration of cuff inflation may be about 2 seconds, and the duration of cuff deflation may be about 1 second. In embodiments of pulses, the duration of cuff inflation may be about 3 seconds, and the duration of cuff deflation may be about 1 second.

Devices and systems disclosed herein are configured to, and may be used to, deliver a "pulse" or a plurality of "pulses" to a digit of a subject. Methods disclosed herein comprise delivery of a "pulse" or of a plurality of "pulses" to a digit of a subject. In embodiments, pulses may be delivered to a digit at a particular frequency; in embodiments, pulses may be delivered to a digit at two or more frequencies; in embodiments, pulses may be delivered to a digit at irregular intervals; in embodiments, pulses may be delivered to a digit at random intervals.

As used herein, the term "tourniquet" and the phrase "to tourniquet the patient's finger" refer to application of pressure (e.g., application of pressure to a digit) effective to reduce or prevent blood flow out of the digit. Constriction of a digit, as may be effected, for example, by manual squeezing of a digit by two or more fingers of a technician's hand, can reduce or prevent blood flow out of the squeezed digit so that blood collects in the distal portion of the digit (the portion farther from the palm of the hand or ball of the foot) aiding in collection of a blood sample from that digit after lancing that digit.

An automatic sample analysis device or system may be configured to receive the sample, whether it be directly from a subject, from a bodily fluid collector, or from any other mechanism. A sample may be placed in a container for transport to another location; for example, a sample may be placed in a container for transport to an automatic sample analysis device or system at a different location than the sample collection location. A sample in a container may be placed in a cartridge for loading on an automatic sample analysis device or system for processing, for analysis, or both. In embodiments, cartridges containing a sample in a container may also contain reagents for use in analyzing the sample. A sample may be placed within an automatic sample analysis device or system. A sample collection unit of the device may be configured to receive the sample. In some embodiments, a sample may be provided directly to an automatic sample analysis device or system, or a vessel or component may be used as a conduit or means for providing a sample to an automatic sample analysis device or system.

Methods, devices and systems for sample analysis may be used to perform assays on a sample, or samples, in order to detect, determine, or quantify some characteristic of a sample (such as detecting whether or not the sample contains a particular analyte, or such as determining the concentration of a particular analyte present in the sample). In an assay, a sample may be prepared for use, and may be used, in the assay in ways determined by the nature of the target analyte and by the nature and amount of sample available for use in the assay. Steps useful in preparing a sample for use in an assay may be termed "processing" steps, while steps which make, or are closely linked to making, measurements regarding the presence, or amount, or concentration of a target analyte may be termed "analyzing" steps.

Thus, sample analysis may include both processing steps and analyzing steps.

Sample analysis includes processing of a sample, or portion thereof, whether diluted on undiluted. Processing may include, for non-limiting example, providing, storing, transporting, warming, cooling, freezing, filtering, coagulating, separating, centrifuging, diluting, preserving, and other steps.

Sample analysis also includes analyzing a sample, or portion thereof, whether diluted on undiluted. Analyzing may include, for non-limiting example, reacting, hybridizing, binding, illuminating, detecting, comparing (e.g., to a standard curve), subtracting (e.g., values obtained from a blank), and other steps.

Some steps, such as mixing, sonicating, labeling, incubating, chelating, and other steps, may be considered processing steps, or may be considered analyzing steps, or both.

As used herein, a "technician" or a "user" refers to the person operating the automatic pressure application device or system as disclosed herein for use on a patient to collect a fingerstick blood sample.

As used herein, a "patient" or a "subject" is a person from whom the blood sample is being collected and thus on which devices and systems disclosed herein is being used. A blood sample may be collected from a patient for any purpose, including, for example, for a routine clinical check-up, for screening purposes, for diagnostic purposes, for confirmatory purposes, for monitoring purposes, for purposes of determining the effect or metabolism of drugs or other compounds or agents taken by the patient, for purposes of determining the amount or dose of drugs or other compounds or agents to be administered to the patient, to determine the suitability for drugs or treatments contemplated for the patient, and for other reasons.

As used herein, an "adult" refers to an individual whose age is greater than 12 years of age. A patient may be an adult patient. A fingerstick sample is typically collected from a finger (and typically a fingertip) of an adult patient. In embodiments, a fingerstick sample taken from an adult may be obtained from a toe, or from another portion of the body.

As used herein, a pediatric application or a pediatric use is one for children, i.e., individuals of between 2 and 12 years of age. A patient may be a pediatric patient (i.e., may be between 2 and 12 years of age). In embodiments, a fingerstick sample taken from a pediatric patient may be obtained from a toe, or from a heel, or from another portion of the body.

As used herein, an infant is a person of less than 2 years of age. A patient may be an infant patient. In embodiments, a fingerstick sample taken from an infant may be obtained from a finger, or from a heel, or from a toe, or from another portion of the infant's body.

As used herein, "distal" refers to locations on a digit farther away from the base of the digit, while "proximal" refers to locations on a digit closer to the base of the digit, where the base of a digit is the palm of the hand for a finger, and is the region near the ball or arch of the foot for a toe. For example, the tip of a finger is a distal portion of a finger, and the base of a finger is a proximal portion of the finger (e.g., is proximal to the palm of the hand). For example, the tip of a toe is a distal portion of a toe, and the base of a toe is a proximal portion of the toe (e.g., is near to the ball of the foot). Thus, as used herein, a proximal portion of a digit is closer to the palm of the hand or to the ball of the foot than a distal portion of that digit.

As used herein, a "redraw" is a repetition of a sample collection attempt; such an attempt may be by using a new lancet on a finger, by using a new needle on a vein, by using a new needle on an artery, or by other means.

As used herein, the term "point of service location" refers to locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

As used herein, a Patient Service Center (PSC) is a retail location at which sample collections are or may be performed.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

Fingerstick Blood Collection

Applicant discloses herein methods, devices, systems, and kits for fingerstick blood collection. In embodiments, some or all of such blood collection may comprise automated fingerstick blood collection. These methods, devices, systems, and kits are simple and straight-forward to use. These methods, devices, systems, and kits are designed so that no extensive amount of training or experience are required for their successful use in obtaining fingerstick samples from subjects. For example, in embodiments, methods, devices, systems, and kits disclosed herein are designed for use by technicians with little or no prior technical or medical experience. Thus, the methods, devices, systems, and kits disclosed herein are designed for use by sophisticated and by unsophisticated technicians and phlebotomists, and offer advantages including ease of use and wide applicability.

Typically, fingerstick blood sample collection is performed quickly in order to obtain the blood sample before partial or complete clotting of the lancing site occurs; quick collection (e.g., less than about 100 seconds, or less than about 90 seconds, or less than about 80 seconds, or less than about 70 seconds, or less than about 60 seconds) provides a fingerstick blood sample of sufficient volume and quality for diagnostic processing. In some instances, collecting blood from a fingerstick at times later than about 80 seconds may lead to collection of blood of insufficient quality or integrity for proper blood analysis. In embodiments, collecting blood from a fingerstick within a time period of less than about 80 seconds, or less than about 70 seconds, or less than about 60 seconds, provides blood of sufficient quality and integrity for proper blood analysis. For example, coagulation of blood increases over time following wound formation, and so may occur in increasing amounts over time after lancing, reducing (negatively impact) the quality of the sample (due to increasing amounts of coagulation or other sample degradation), and may reduce (negatively impact) the integrity of the blood sample as coagulation increases and the relative amounts of plasma or serum in the whole blood alter over time after lancing to obtain the fingerstick blood sample. For further example, excessive leakage of interstitial fluid, as may occur in increasing amounts over time after lancing, may contaminate a blood sample and may reduce (negatively impact) the quality of the sample (possibly altering analyte concentrations, or in other ways reducing the quality of the blood sample), and may reduce (negatively impact) the integrity of the blood sample as increasing amounts of contaminating fluid is mixed in with the blood obtained from the fingerstick.

Manual gripping techniques in which pressure is applied cyclically to the finger during collection following lancing may be used to generate blood drops for collection into a collection tube, or other sample collection device. Continuous application of pressure to the digit (e.g., constriction of a digit) is believed to improve fingerstick blood collection by increasing blood volume in distal portions of a digit after a sufficient amount of time following application of pressure. Cyclic application of pressure to the digit is believed to improve fingerstick blood collection by increasing blood volume in distal portions of a digit during the time soon after lancing following continuous application of pressure. Such increased blood volume may aid in the collection of sufficient amounts of blood soon after lancing and so avoid or reduce problems which may arise from coagulation, leakage of interstitial fluid, or other problems which lead to reduced quality and reduced integrity of fingerstick blood samples. Such cyclic application of pressure to the digit during fingerstick blood collection is also believed to reduce discomfort and pain that may otherwise be felt by a subject during or after collection of a fingerstick blood sample. Although effective, manual gripping techniques require training and practice to execute well.

For example, manual gripping techniques for cyclic application of pressure to a digit during fingerstick blood sample collection require a certain amount of dexterity and coordination. Training and practice are desired in order to learn to properly perform such manual gripping techniques for cyclic application of pressure to a digit during fingerstick blood sample collection. Improper application of manual gripping techniques for cyclic application of pressure to a digit during fingerstick blood sample collection may reduce blood flow into the digit and lead to collection of an insufficient volume of blood, or may lead to excessive coagulation of blood during blood collection, or may allow contamination of the blood sample with excessive amounts of interstitial fluid, or other problems. Such problems may require that a sample be discarded, and another sample collected; such a "redraw" may be unexpected by the subject, who may find such a "redraw" uncomfortable or undesirable. Discarding a blood sample is wasteful, and obtaining a replacement sample takes further time and expense. In addition, manual application of pressure to a digit during fingerstick blood sample collection may, on occasion, require the technician to use their non-dominant hand, and may possibly lead to repetitive motion injuries with long-term use of such manual grip techniques. Although the collection time may be an important parameter with regard to sample quality, manual techniques typically provide no feedback to the technician regarding how long collection is taking, and may be inconsistent in their application and in their results. Consequently, when pressure is applied to a digit using manual techniques, sample quality issues related to collection speed can be difficult to identify or trace.

Applicant discloses herein devices and systems for automated application of pressure to a digit. Applicant discloses herein devices and systems for automated application of pressure to a digit which include automated cyclic application of pressure to a digit during fingerstick blood sample collection. The methods, devices, systems, and kits disclosed herein automate the process of cyclic application of pressure to a digit during fingerstick blood collection. These automated devices and methods are believed to improve the practice of cyclic application of pressure to a digit as compared to manual methods of cyclic application of pressure to a digit during fingerstick blood collection. These automated devices and methods are believed to provide more consistent and more reliable cyclic application of pressure to a digit as compared to manual methods of cyclic application of pressure to a digit during fingerstick blood collection. These automated devices, systems, kits, and methods of cyclic application of pressure to a digit during fingerstick blood collection are believed to provide better fingerstick blood samples than are typically obtained using manual methods of cyclic application of pressure to a digit during fingerstick blood collection. Such better fingerstick blood samples may be collected sooner (i.e., sufficient volume of blood may be collected sooner than would typically be the case with manual methods of cyclic application of pressure to a digit during fingerstick blood collection). Such better fingerstick blood samples may have less coagulation (i.e., as compared to such a fingerstick blood sample collected using manual methods of cyclic application of pressure to a digit during fingerstick blood collection). Such better fingerstick blood samples may have less contamination by interstitial fluid (i.e., as compared to such a fingerstick blood sample collected using manual methods of cyclic application of pressure to a digit during fingerstick blood collection). Such better fingerstick blood samples may be of higher quality, or a greater integrity (i.e., as compared to such a fingerstick blood sample collected using manual methods of cyclic application of pressure to a digit during fingerstick blood collection). The use of automated application of pressure to a digit may further allow a technician to focus attention on positioning of a sample collection device and on collecting a sample without also having to focus on coordinated application of pressure to the subject. Thus, the present automated devices, systems, kits, and methods are believed to provide advantages over manual methods of cyclic application of pressure to a digit during fingerstick blood collection.

Devices and Systems

Applicant discloses herein devices, systems, methods, and kits useful for collecting fingerstick blood samples from a digit (e.g., from a finger or toe). In embodiments, devices for collecting fingerstick blood samples provide automated pressure cycling for collection of blood during a fixed collection time period. In embodiments, such automated pressure cycling is provided by an inflatable cuff which fits around a digit, and may be inflated and deflated repeatedly during at least part of the collection time period. In embodiments, devices for collecting fingerstick blood samples provide digit warming as well as automated pressure cycling for collection of blood during a fixed collection time period. In embodiments, devices for collecting fingerstick blood samples provide digit warming and digit lancing as well as automated pressure cycling for collection of blood during a fixed collection time period.

In embodiments, systems for collecting fingerstick blood samples provide automated pressure cycling for collection of blood during a fixed collection time period. In embodiments, such automated pressure cycling is provided by an inflatable cuff which fits around a digit, and may be inflated and deflated repeatedly during the collection time period. In embodiments, systems for collecting fingerstick blood samples provide digit warming as well as automated pressure cycling for collection of blood during a fixed collection time period. In embodiments, systems for collecting fingerstick blood samples provide digit warming and digit lancing as well as automated pressure cycling for collection of blood during a fixed collection time period.

In embodiments, a device having features as disclosed herein comprises a cuff configured to at least partially encircle a human digit; a pressure source configured to inflate said cuff effective to apply pressure to a digit disposed at least partially within the cuff; and a timing mechanism configured to provide a signal at the end of a period of time, where said period of time is a desired period of time for collecting a fingerstick blood sample from said digit. In embodiments, a timing mechanism of such a device having features as disclosed herein further provides a signal at the beginning of said period of time. In embodiments, a signal provided by such a timing mechanism may be a signal selected from an audible signal, a visible signal, and a tactile signal. In embodiments, a timing mechanism signal may be a beep or a tone. In embodiments, a timing mechanism signal at the beginning of a period of time may be different than the timing mechanism signal provided at the end of the period of time.

In embodiments, such a period of time is at least about one minute in duration. In embodiments, such a period of time is 60 seconds in duration. In embodiments, such a timing mechanism is configured to end the inflation of said cuff at the end of said period of time. In embodiments, a cuff of a device having features as disclosed herein may be configured to be inflated to a maximum pressure of about 300 mm of mercury of pressure. In embodiments, a cuff of a device having features as disclosed herein may include a warming mechanism configured to warm a digit disposed within said cuff. In embodiments, a timing mechanism may be configured to indicate a warming period during which a digit is to be warmed. In embodiments, a warming period is a period of time of about 45 seconds or more. In embodiments, a cuff of a device having features as disclosed herein may comprises a plurality of lobes, wherein each lobe may be inflated independently of the other lobe or lobes.

In embodiments, a device having features as disclosed herein may include a lancing mechanism. In embodiments, such a lancing mechanism may be configured to puncture a digit effective to make a wound or incision in said digit providing blood for sample collection. In embodiments, such a lancing mechanism may be configured to lance a digit disposed within said cuff, without contacting the cuff. In embodiments, such a lancing mechanism may be configured to lance a digit disposed within said cuff, without affecting the cuff, including without puncturing the cuff. In embodiments, a lancing mechanism includes a needle, a blade, or other lancing implement configured to produce a puncture or incision in the skin of a subject effective to release capillary blood from the resulting wound. In embodiments, such a wound may be about 1 to 2 millimeters (mm) in depth for an adult subject, and may be about 0.5 to 1 mm in depth for an infant.

In embodiments, a device having features as disclosed herein may include an automated sample collection device configured to receive a blood sample obtained from said digit. In embodiments, a device having features as disclosed herein may include an automated sample analysis device configured to dilute a blood sample obtained from said digit. In embodiments, a device having features as disclosed herein may include an automated sample analysis device configured to process a blood sample obtained from said digit. In embodiments, a device having features as disclosed herein may include an automated sample analysis device configured to analyze a blood sample obtained from said digit. In embodiments, such an automated sample analysis device may be configured to detect, or to measure the concentrations of, a plurality of analytes in said blood sample obtained from said digit. In embodiments, such an automated sample analysis device is configured to detect, or to measure the concentrations of, at least two analytes of different analyte types in said blood sample obtained from said digit, wherein said analyte types consist of nucleic acid analytes, peptide analytes, small molecule analytes, and cellular markers.

In embodiments, a device having features as disclosed herein may include a communication unit effective to transmit data obtained from said blood sample. In embodiments, such a communication unit may be effective to transmit data obtained from said a blood sample. In embodiments, such a communication unit is effective to transmit raw data obtained from processing or analysis of the blood sample. In embodiments, such a communication unit is effective to transmit analysis results obtained from analysis of the blood sample.

In embodiments, a device having features as disclosed herein may include a warming mechanism configured to warm a digit disposed within said cuff, and a lancing mechanism configured to puncture a digit effective to make a wound or incision in said digit providing blood for sample collection. In embodiments, a device having features as disclosed herein may include a pressure-interruption switch. A pressure interruption switch is configured to interrupt inflation of a cuff, and may be configured to allow deflation of a cuff. In embodiments, a pressure interruption switch may be operably connected to a source of pressure, or between a source of pressure and an inflatable cuff, effective that operation of the pressure interruption switch prevents pressure flow to the cuff when the switch is activated. In embodiments, a pressure interruption switch may be operably connected to a pump, effective that operation of the pressure interruption switch stops operation of the pump when the switch is activated. In embodiments, a pressure interruption switch may be operably connected to a conduit connecting a source of pressure to a cuff, effective to block or occlude the conduit to prevent pressure flow to the cuff when the switch is activated. In embodiments, a pressure interruption switch may be operably connected to a relief valve, effective that operation of the pressure interruption switch opens the relief valve and allows deflation of the cuff when the switch is activated. In embodiments, a pressure-interruption switch is a foot pedal.

In embodiments, a system having features disclosed herein may include a device having features as disclosed herein, and an automated sample collection device configured to collect a blood sample from a puncture wound in a digit. In embodiments, a system having features disclosed herein may include a device having features as disclosed herein, and an automated sample analysis device configured to dilute a blood sample. In embodiments, a system having features disclosed herein may include a device having features as disclosed herein, and an automated sample analysis device configured to process a blood sample. In embodiments, a system having features disclosed herein may include a device having features as disclosed herein, and an automated sample analysis device configured to analyze a blood sample.

In embodiments, a system having features disclosed herein may include a device having features as disclosed herein, an automated sample collection device configured to collect a blood sample from a puncture wound in a digit, and a communication unit effective to transmit data obtained from said a blood sample. In embodiments, a system having features disclosed herein may include a device having features as disclosed herein, an automated sample analysis device configured to dilute a blood sample, and a communication unit effective to transmit data obtained from said a blood sample. In embodiments, a system having features disclosed herein may include a device having features as disclosed herein, an automated sample analysis device configured to process a blood sample, and a communication unit effective to transmit data obtained from said a blood sample. In embodiments, a system having features disclosed herein may include a device having features as disclosed herein, an automated sample analysis device configured to analyze a blood sample, and a communication unit effective to transmit data obtained from said a blood sample.

Applicant discloses herein devices and systems including a cuff and a source of pressure. A cuff is configured to contact and to at least partially encircle a digit (or other body part) of a subject. In embodiments, a cuff may be configured to contact and to at least partially encircle a digit (or other body part) while leaving at least a portion of the digit (or other body part) exposed for lancing by a lancet, needle, blade, or other lancing device. In embodiments, a source of pressure may include a pump, or a reservoir of compressed gas, or other pressure source. A pump may provide air pressure, or liquid pressure, or otherwise provide pressure effective to inflate a cuff. A pump may be or include a rotary pump, a peristaltic pump, a piston, or other source of pressure. A cuff and a source of pressure are operably connected, e.g., via conduit, which conduit may regulate the pressure provided to the cuff by the pressure source (e.g., may prevent, allow, or modulate the application and amount of pressure provided to the cuff). A conduit is typically flexible, and may be hinged, or include joints or other elements providing mobility and allowing ease of placement of a cuff attached to such a conduit. In embodiments, devices as disclosed herein may include a valve, or a plurality of valves, effective control or modulate the application and amount of pressure provided to the cuff. In embodiments, devices as disclosed herein may include a pressure regulator effective control or modulate the application and amount of pressure provided to the cuff. Application of pressure to the cuff by the pressure source is effective to inflate the cuff; when a cuff is in place on or around a digit (or other body part), such inflation is effective to compress or constrict at least a portion of the digit or other body part.

For example, a cuff may be placed on a distal portion of a finger (or toe) of a subject, leaving at least about 5 millimeters (mm) or at least about 10 mm of skin exposed on a distal portion of the finger (or toe) and available for lancing. The cuff may be inflated, constricting the finger (or toe), so as to reduce or prevent blood flow out of a distal portion of the finger (or toe), allowing blood to collect in the distal portion of that finger (or toe). Such collection of blood in the distal portion of that finger (or toe) may be observed by a reddening, or deepening in color, of that portion of that finger (or toe). Lancing of that distal portion of that finger (or toe) provides blood for fingerstick blood sample collection. Warming of the finger (or toe) prior to constriction of the distal portion of that finger (or toe) may be effective to increase the amount of blood collecting in that distal portion (as compared to the amount collecting in that distal portion without prior warming) for fingerstick blood sample collection, may increase blood flow out of a wound made by lancing that finger (or toe), and may be effective to reduce the amount of time required to collect a desired amount of blood from that wound following lancing.

In embodiments, such a cuff has a warming element effective to warm finger in contact with the cuff, or enclosed or encircled by the cuff. A digit in contact with, or in place within, a cuff may be warmed prior to inflation of the cuff. A digit in contact with, or in place within, a cuff may be warmed during inflation of the cuff, and may be warmed while the cuff remains inflated, or during cycles of cuff inflation.

In embodiments, lancing of a digit may be performed while the digit is in place within a cuff. Typically, such lancing may occur while the cuff is inflated; in embodiments, such lancing occurs following a period of cuff inflation. In embodiments, such lancing is performed on a digit in place within an inflated cuff after the digit has noticeably deepened or reddened in color. In embodiments, such lancing is performed on a digit in place within a cuff at least about 5 seconds following inflation of the cuff. In embodiments, such lancing is performed on a digit in place within a cuff at least about 10 seconds following inflation of the cuff. In embodiments, such lancing is performed on a digit in place within an inflated cuff following a signal from the device indicating that sufficient inflation time has passed and lancing may proceed. In embodiments, such a signal is an audible signal, such as a beep or a tone. In embodiments, such lancing is automatically performed on a digit in place within an inflated cuff by an automated lancing mechanism.

In embodiments, collection of a fingerstick blood sample follows lancing of the digit. In embodiments, such collection of a fingerstick blood sample may be performed manually. In embodiments, such collection of a fingerstick blood sample may be performed following a signal from the device indicating that blood collection may proceed. In embodiments, such a signal is an audible signal, such as a beep or a tone. In embodiments, such collection of a fingerstick blood sample may be performed automatically by an automated sample collection device, or by an automated sample collection system.

Applicant discloses herein devices and systems including a cuff, a pressure source, and a timing mechanism, wherein the cuff is configured to contact and to at least partially encircle a digit of a subject, and to apply pressure to that digit for a period of time. The period of time during which a cuff may apply pressure to a digit may be determined by the timing mechanism, or a timing mechanism may provide a timing signal to aid an operator in identifying a start time for application of pressure, a duration for application of pressure, a stop time for application of pressure, or combinations thereof. Thus, in embodiments, a timing signal may be provided to indicate the beginning of the blood collection period; to indicate the end of the blood collection period; and timing signals may be provided indicating the beginning of the blood collection period and the end of the blood collection period. In embodiments, a timing signal may be provided to indicate the beginning of the warming period; to indicate the end of the warming period; and timing signals may be provided indicating the beginning of the warming period and the end of the warming period. In embodiments, a timing signal may be provided to indicate the beginning of pressure application; to indicate the end of pressure application; and timing signals may be provided indicating the beginning and end of the time period for pressure application. In embodiments, the time period for pressure application is the time period for continuous pressure application; in embodiments, the time period for pressure application is the time period for cyclic pressure application. In embodiments, a timing signal may be provided to indicate the time of beginning cycling of pressure application; to indicate the time of ending cycling of pressure application; and, in embodiments, timing signals may be provided indicating the beginning and end of the time period for cyclic pressure application. In embodiments, a timing signal may be provided to indicate the proper time to lance a digit and at other times.

Applicant notes that the amount of time taken to collect a fingerstick blood sample may affect the quality of the sample. Collection of blood for a fingerstick blood sample is preferably performed soon after lancing a digit to provide a fingerstick wound from which to collect the blood sample. Blood flowing from a digit from a fingerstick wound is capillary blood; such blood is suitable for use in a fingerstick blood sample so long as the blood is not degraded or compromised in quality. Degradation of a fingerstick blood sample occurs, for example, as the blood becomes coagulated; as hemolysis occurs in the blood sample; as interstitial fluid from tissue around the wound mixes with the blood sample. Such degradation is non-existent or negligible at short periods of time following lancing of the digit. However, over a period of time, the blood flowing from the fingerstick wound becomes degraded, and becomes of lower quality, as indicated above.

A cuff having features as disclosed herein may fit at least partially around a digit, and may completely encircle a digit; in embodiments, the cuff is an inflatable cuff. In embodiments, a cuff may at least partially encircle a digit and leave a distal portion of the digit uncovered, effective to provide access by a lancet to skin of the digit. In embodiments, a cuff may completely encircle a digit and leave a distal portion of the digit uncovered, effective to provide access by a lancet to skin of the digit. In embodiments, a cuff may leave a proximal portion of the digit uncovered. When inflated in place on or around a digit, a cuff is effective to constrict a portion of the digit and to limit blood flow in the constricted portion. In embodiments, an inflated cuff, when in place on or around a digit, the cuff is effective to limit blood flow into the constricted portion. In embodiments, an inflated cuff, when in place on or around a digit, the cuff is effective to limit blood flow out of the constricted portion. Such a cuff may completely encircle a digit when in place on the digit; or may partially encircle the digit when in place on the digit. In embodiments, such a cuff may be configured to operate with digits ranging in size from about 75 mm to about 3.5 centimeter (cm) in diameter. In embodiments, such a cuff may be configured to operate with digits ranging in size from about 1 cm to about 3 cm in diameter; and may be configured to operate with digits ranging in size from about 1.3 cm to about 2.5 cm diameter.

A cuff configured to operate with digits of a particular size or size range is sized to accommodate a digit of that particular size or size range: that is, such a cuff (when deflated) has an internal diameter that is at least that size, or can be stretched to that size, effective to allow placement of the cuff around a digit of about that particular size (when deflated). In embodiments, a cuff has an internal diameter of between about 1 centimeter (cm) and about 3 cm, or has an internal diameter of between about 1.3 centimeter (cm) and about 2.5 cm (where an internal diameter is measured across the open area demarked by the cuff). Internal diameter is determined when the cuff is deflated. When inflated, the internal diameter of a cuff is smaller than the internal diameter of the cuff when deflated.

Applicant further discloses herein devices and systems including a cuff, a source of pressure, a means to pulse the application of pressure, and a timing mechanism, wherein the cuff is configured to contact and to at least partially encircle a digit of a subject, and to apply pressure to that digit for a period of time. Applicant further discloses herein devices and systems including a cuff, a source of pressure, a means to pulse the application of pressure, and a timing mechanism, wherein the cuff is configured to contact and to at least partially encircle a digit of a subject, and to apply pressure pulses of desired duration, of desired frequency, or both, to that digit for a period of time. In embodiments, such a timing mechanism may be configured to alert a user to the expiration of a period of time. A user may be alerted by an audible signal, a visible signal, a vibration, or other means and signals. In embodiments, such an audible signal may be a beep or a tone. In embodiments, such a timing mechanism may be configured to end the application of pressure to a digit upon the expiration of a period of time. In embodiments, such a timing mechanism may be operably connected with the pressure source, or with other elements of the devices disclosed herein, so as to end the application of pressure pulses to a digit upon the expiration of a period of time. In embodiments, such a period of time is an optimal period of time for collecting blood flowing from a digit for use in a blood sample. In embodiments, such a period of time is a period of time during which blood flowing from a digit is suitable for use in a blood sample. In embodiments, such a period of time is a period of time during which blood flowing from a digit is suitable for use in clinical analysis. In embodiments, such a period of time is a period of time during which blood flowing from a digit has not significantly degraded as compared to a blood sample suitable for use in clinical analysis. In embodiments, such a period of time is a period of time during which blood flowing from a digit has suitable integrity for use in a blood sample. In embodiments, such a period of time is a period of time during which blood flowing from a digit has suitable quality for use in a blood sample. In embodiments, such a period of time is a period of time during which blood flowing from a digit is not substantially coagulated. In embodiments, such a period of time is a period of time during which blood flowing from a digit is not substantially mixed with interstitial fluid.

In embodiments, such devices and systems may further include a pressure-interruption switch, for use by an operator of the devices and systems, that is configured to pause or stop the application of pressure. In embodiments, such a pressure-interruption switch may be a foot-pedal switch. In embodiments, such a pressure-interruption switch may be a hand-operated switch. In embodiments, such a pressure-interruption switch may be a voice-activated switch. In embodiments, such a pressure-interruption switch may be a light-activated switch. In embodiments, such a pressure-interruption switch may be operably connected to the pressure source, or to the conduit connecting the pressure source to the cuff, or both, effective to stop the pump, or block flow of pressurized gas, or otherwise interrupt the provision of pressure to the cuff, temporarily stopping inflation of the cuff. In embodiments, such a pressure-interruption switch may allow deflation of the cuff, by, e.g., opening a relief valve in the cuff, the conduit, or elsewhere, allowing pressure or pressurized gas to escape, allowing the cuff to deflate, or by other means. In embodiments, such a pressure-interruption switch may both interrupt the provision of pressure to the cuff, and allow deflation of the cuff.

In embodiments, such devices and systems may further include a warming mechanism configured to warm a digit. In embodiments, such a warming mechanism may be configured to warm at least a portion of a digit within, or in contact with, a cuff. In embodiments, such a warming mechanism may be disposed on or within a cuff. In embodiments, such a warming mechanism, when disposed on or in contact with a digit, may contact a larger portion of the surface of a digit than does a cuff disposed on or in contact with that digit. In embodiments, such a warming mechanism may be configured to apply warmth to a digit prior to the application of pressure to the digit by the cuff. In embodiments, such a warming mechanism may be configured to apply warmth to a digit during the application of pressure to the digit by the cuff.

In embodiments, such devices and systems may be configured to, and may be used to, apply pressure to a digit prior to manual lancing of that digit. In embodiments, such devices and systems may be configured to, and may be used to, warm a digit and to apply pressure to a digit prior to manual lancing of that digit. In embodiments, such devices and systems may be configured to, and may be used to, apply pressure to a digit prior to manual collection of a fingerstick blood sample from that digit. In embodiments, such devices and systems may be configured to, and may be used to, warm a digit and to apply pressure to a digit prior to collection of a fingerstick blood sample from that digit.

In embodiments, such devices and systems may further include a lancing mechanism configured to puncture a digit effective to make a wound or incision in a digit for providing blood for sample collection. In embodiments, such a lancing mechanism may be configured to lance a portion of a digit that is not covered by a cuff. In embodiments, such a lancing mechanism may be configured to lance a distal portion of a digit. In embodiments, such a lancing mechanism may be configured to lance a digit following application of pressure to the digit by a cuff. In embodiments, such a lancing mechanism may be configured to lance a digit following application of warmth to the digit by a warming mechanism. In embodiments, such a lancing mechanism may be configured to lance a digit following application of warmth to the digit by a warming mechanism and following application of pressure to the digit by a cuff. In embodiments, a lancing mechanism includes a needle, a blade, or other lancing implement configured to produce a puncture or incision in the skin of a subject effective to release capillary blood from the resulting wound. In embodiments, such a wound may be about 1 to 2 millimeters (mm) in depth for an adult subject, and may be about 0.5 to 1 mm in depth for an infant.

In embodiments, such devices and systems may be configured to, and may be used to, apply pressure to a digit prior to automatic lancing of that digit, and prior to manual collection of a fingerstick blood sample from that digit. In embodiments, such devices and systems may be configured to, and may be used to, warm a digit and to apply pressure to a digit prior to automatic lancing of that digit, and prior to collection of a fingerstick blood sample from that digit.

In embodiments, such devices and systems may further include a blood sample collection mechanism configured to collect blood flowing from a puncture or incision in a digit. In embodiments, such a blood sample collection mechanism may be configured to collect blood flowing from a puncture or incision in a digit following application of pressure to the digit by a cuff. In embodiments, such a blood sample collection mechanism may be configured to collect blood flowing from a puncture or incision in a digit following application of warmth to the digit by a warming mechanism. In embodiments, such a blood sample collection mechanism may be configured to collect blood flowing from a puncture or incision in a digit following application of warmth to the digit by a warming mechanism and following application of pressure to the digit by a cuff. In embodiments, lancing of a digit may be performed manually, or may be performed by a device, including by a device having features as disclosed herein.

In embodiments, such devices and systems may further include an automated sample analysis device or an automated sample analysis system. Such an automated sample analysis device or automated sample analysis system is configured to receive a blood sample, and to perform at least one blood analysis test on the sample. In embodiments, such automated sample analysis devices or automated sample analysis systems may directly receive blood from a digit following application of pressure by a cuff and following lancing of the digit contacted by, or encircled by, a cuff of a device or system as disclosed herein. In embodiments, such automated sample analysis devices or automated sample analysis systems may receive blood collected from a digit following application of pressure by a cuff and following lancing of the digit contacted by, or encircled by, a cuff of a device or system as disclosed herein, where such blood is transferred from a device or system comprising a cuff. In embodiments, such a transfer of blood is effected within a single housing which includes a cuff, a pressure source, and a timer as well as an automated sample analysis device or automated sample analysis system. In embodiments, such a transfer of blood is effected between a device or system which includes a cuff, a pressure source, and a timer as disclosed herein, and an automated sample analysis device or automated sample analysis system, where the device or system which includes a cuff, a pressure source, and a timer is separate from the automated sample analysis device or automated sample analysis system. In embodiments, such devices and systems may include a transport mechanism or transport system effective to transport a blood sample from a blood collection mechanism to an automated sample analysis device or an automated sample analysis system.

In embodiments, a device or system as disclosed herein, which comprises an automated sample analysis device or an automated sample analysis system in addition to a cuff and a pressure source, may also include one or more of a pressure-interruption switch, a timing mechanism, a warming mechanism, a lancing mechanism, a blood collection mechanism, and other mechanisms.

In embodiments, a device or system as disclosed herein, which comprises an automated sample analysis device or an automated sample analysis system in addition to a cuff, a pressure source, and a timer, may also include one or more of a pressure-interruption switch, a warming mechanism, a lancing mechanism, a blood collection mechanism, and other mechanisms.

In embodiments, a device or system as disclosed herein comprising a cuff and a pressure source, may also include one or more of a pressure-interruption switch, a timing mechanism, a warming mechanism, a lancing mechanism, a blood collection mechanism, and other mechanisms, and may in addition include a communication unit effective to transmit data regarding a blood sample. In embodiments, a device or system as disclosed herein which comprises an automated sample analysis device or an automated sample analysis system in addition to comprising a cuff and a pressure source, may also include one or more of a pressure-interruption switch, a timing mechanism, a warming mechanism, a lancing mechanism, a blood collection mechanism, and other mechanisms.

In embodiments, a device or system as disclosed herein comprising a cuff, a pressure source, and a timer, may also include one or more of a pressure-interruption switch, a warming mechanism, a lancing mechanism, a blood collection mechanism, and other mechanisms, and may in addition include a communication unit effective to transmit data regarding a blood sample. In embodiments, a device or system as disclosed herein which comprises an automated sample analysis device or an automated sample analysis system in addition to comprising a cuff, a pressure source, and a timer, may also include one or more of a pressure-interruption switch, a warming mechanism, a lancing mechanism, a blood collection mechanism, and other mechanisms.

The devices and systems disclosed herein may include elements configured to contact a digit and to compress or apply pressure to at least a portion of that digit. In embodiments, devices and systems disclosed herein may include elements configured to encircle a digit and to compress or apply pressure to at least a portion of that digit. In embodiments, devices and systems disclosed herein may include elements configured to contact, or to encircle, or both, a digit and to compress or apply pressure to at least a portion of that digit for a period of time. In embodiments, devices and systems disclosed herein may include elements configured to contact, or to encircle, or both, a digit and to compress or apply pressure to at least a portion of that digit for a plurality of periods of time, wherein said plurality of periods of time may be separated by a time period during which compression or pressure is not applied to the digit. In embodiments, devices and systems disclosed herein may include elements configured to contact, or to encircle, or both, a digit and to repeatedly compress or apply pressure to at least a portion of that digit at a defined frequency of application of compression or pressure; in embodiments, periods of time during which compression or pressure is applied may be separated by time periods during which compression or pressure is not applied to the digit. In some embodiments, the frequency of application of pressure or compression to a digit may be unvarying; and, in other embodiments, the frequency of application of pressure or compression to a digit may vary. In some embodiments, the duration of time periods during which compression or pressure is not applied to the digit may be unvarying; and, in other embodiments, the duration of time periods during which compression or pressure is not applied to the digit may vary.

In embodiments, the devices and systems disclosed herein provide automation of the finger pressurizing process during fingerstick blood collection in order to eliminate the dependency on, and the variability due to, differences between the grip techniques used by different technicians, and due to differences in application of a grip technique by an individual technician as applied to different subjects. The methods, devices, systems and kits disclosed herein are designed to minimize the amount of technician training that may be required to reproducibly extract blood from the finger of a subject during fingerstick blood collection, to control the total time allowed for fingerstick blood collection, and in other ways improve standardization and consistency of the collection process.

Embodiments of the automated fingerstick blood collection methods, devices, systems, and kits disclosed herein include devices, and the use of devices, which provide automated pressure application to a digit (e.g., a finger), with automatic cycling of such pressure between a low pressure (which may include no added pressure, or may include a small amount of pressure application) and a high pressure (which may include a pressure sufficient to completely occlude, and may include a pressure that does not completely occlude, blood flow out of the extremity.

Embodiments of the automated fingerstick blood collection methods, devices, systems, and kits disclosed herein include devices, and the use of devices, which provide 1) automatic application of heat to a digit (e.g., a finger), and 2) automated pressure application to a digit (e.g., a finger), with automatic cycling of such pressure between a low pressure (which may include no added pressure, or may include a small amount of pressure application) and a high pressure (which may include a pressure sufficient to completely occlude, and may include a pressure that does not completely occlude, blood flow out of the extremity.

Embodiments of the automated fingerstick blood collection methods, devices, systems, and kits disclosed herein include devices, and the use of devices, which provide 1) automatic application of heat to a digit (e.g., a finger), 2) automatic lancing of the extremity, and 3) automated pressure application to a digit (e.g., a finger), with automatic cycling of such pressure between a low pressure (which may include no added pressure, or may include a small amount of pressure application) and a high pressure (which may include a pressure sufficient to completely occlude, and may include a pressure that does not completely occlude, blood flow out of the extremity.

Devices, Systems, and Kits

FIG. 1 shows a perspective view of an exemplary device 10 having features as disclosed herein, including a pressure cuff 40 attached to a conduit 38 and thereby to a control unit 12 having a housing 22, the control unit including a pump effective to apply pressure to the cuff under the control of the control unit, and a power cable 34 for connecting a power supply within the housing 22 to a power source (e.g., an electrical cable 34 with plug 35 for connecting to an electrical power outlet).

Figure 2A:
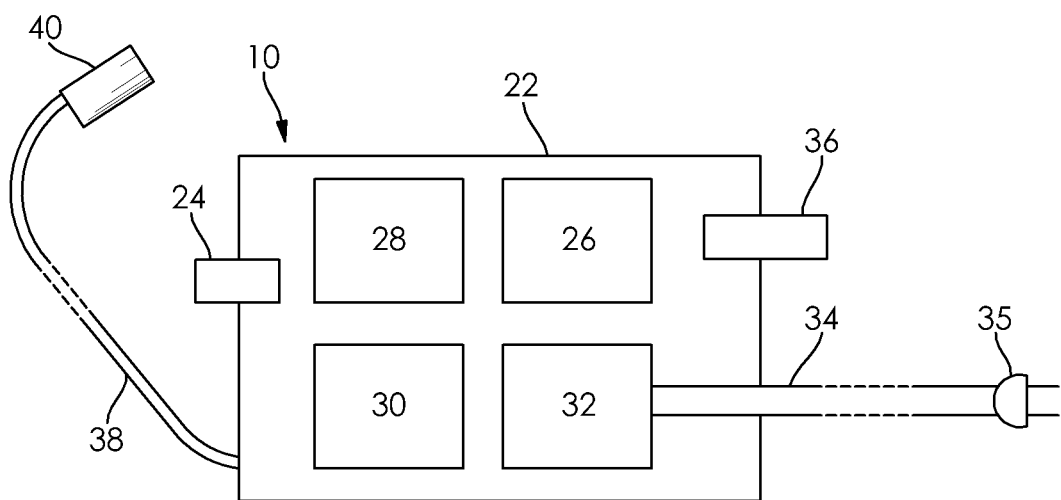
FIG. 2A is a schematic diagram showing elements of an exemplary device as disclosed herein, including a housing with an ON/OFF switch and containing a pressure source connected to a cuff configured to constrict a digit, a timer, a signal source, a power supply connected to a power cable, and a link to an (optional) foot pedal (interrupt switch).

FIG. 2A is a schematic diagram showing elements of an exemplary device 10 as disclosed herein, including a housing 22 with an ON/OFF switch 24 and containing a pressure source 26, a timer 28, a signal source 30, a power supply 32 connected to a power cable 34, and a link to an interrupt switch 36. A conduit 38 connects cuff 40 to the pressure source 26. In embodiments, pressure source 26 may be controlled by, or is under the control of, timer 28. In embodiments, application of pressure to a cuff 40 by pressure source 26 may be interrupted by an interrupt switch 36. An interrupt switch 36 may be configured to be operated with minimal interference with collection of a fingerstick blood sample; for example an interrupt switch 36 may be a foot pedal, which a technician may operate at the same time that technician is collecting blood from a subject without requiring the use of a hand to interrupt pressure application. An interrupt switch 36 configured to interrupt pressure application is optional; some embodiments of the devices disclosed herein may lack an interrupt switch 36.

In operation, pressing the ON/OFF switch 24 may begin timing of a timer 28 and may turn on, or begin, a protocol leading to the turning on of, a pressure source 26 effective to inflate cuff 40. In use, a digit of a subject will be placed within a cuff 40, and inflation of the cuff 40 will constrict the digit placed therein. A signal may be generated upon, or soon after, pressing the ON/OFF switch 24. In embodiments, pressure may be applied to a cuff 40 for a continuous period of time during operation. In embodiments, pressure applied to a cuff 40 may cycle between inflated and deflated conditions. In embodiments, pressure applied to a cuff 40 may cycle between inflated and deflated conditions at a set frequency; or at a variable frequency; or for variable amounts of time. In embodiments, pressure applied to a cuff 40 may be held constant for a period of time, and may subsequently cycle between inflated and deflated conditions for a period of time. In embodiments, pressure applied to a cuff 40 may cycle between inflated and deflated conditions for a period of time, and may subsequently be held constant for a period of time.

Figure 2B:
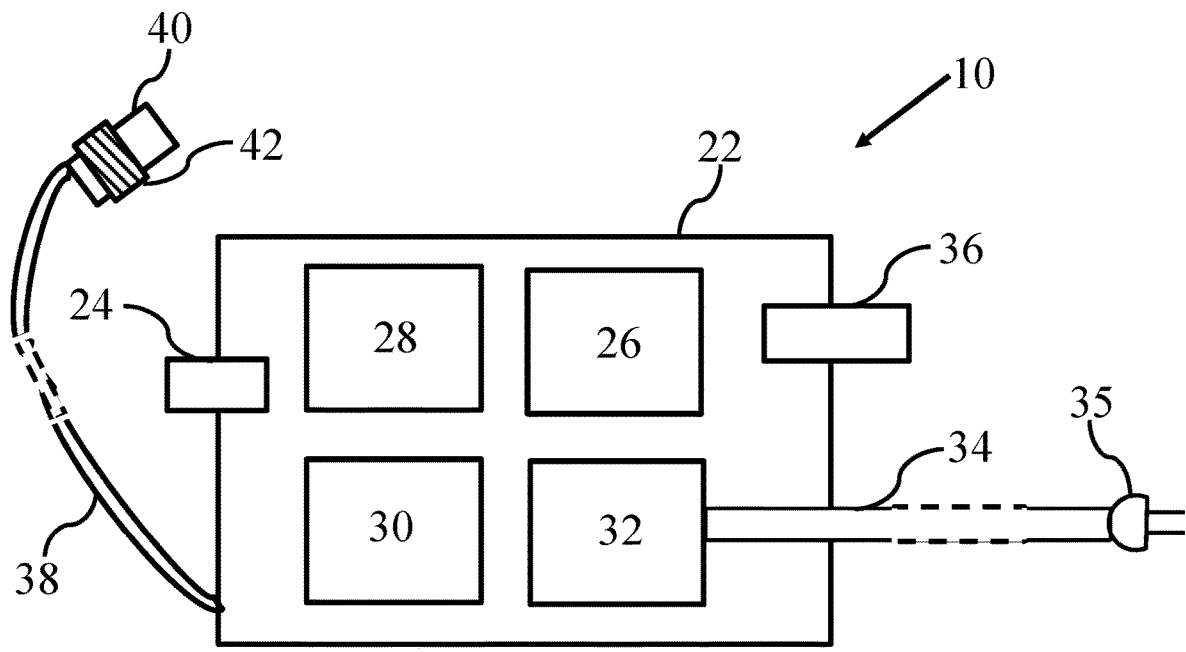
FIG. 2B is a schematic diagram showing elements of an exemplary device as disclosed herein, including a housing with an ON/OFF switch and containing a pressure source connected to a cuff configured to constrict a digit, the cuff including a warming element, a timer, a signal source, a power supply connected to a power cable, and an (optional) link to a foot pedal (interrupt switch). In embodiments, such a device may further include a sample collection device (not shown).

FIG. 2B is a schematic diagram showing elements of an exemplary device 10 as disclosed herein, including a housing 22 with an ON/OFF switch 24 and containing a pressure source 26 connected via a conduit 38 to a cuff 40 configured to constrict a digit, the cuff including a warming element 42, a timer 28, a signal source 30, a power supply 32 connected to a power cable 34, and an (optional) link to a foot pedal (interrupt switch) 36. A conduit 38 connects cuff 40 to the pressure source 26.

Figure 2C:
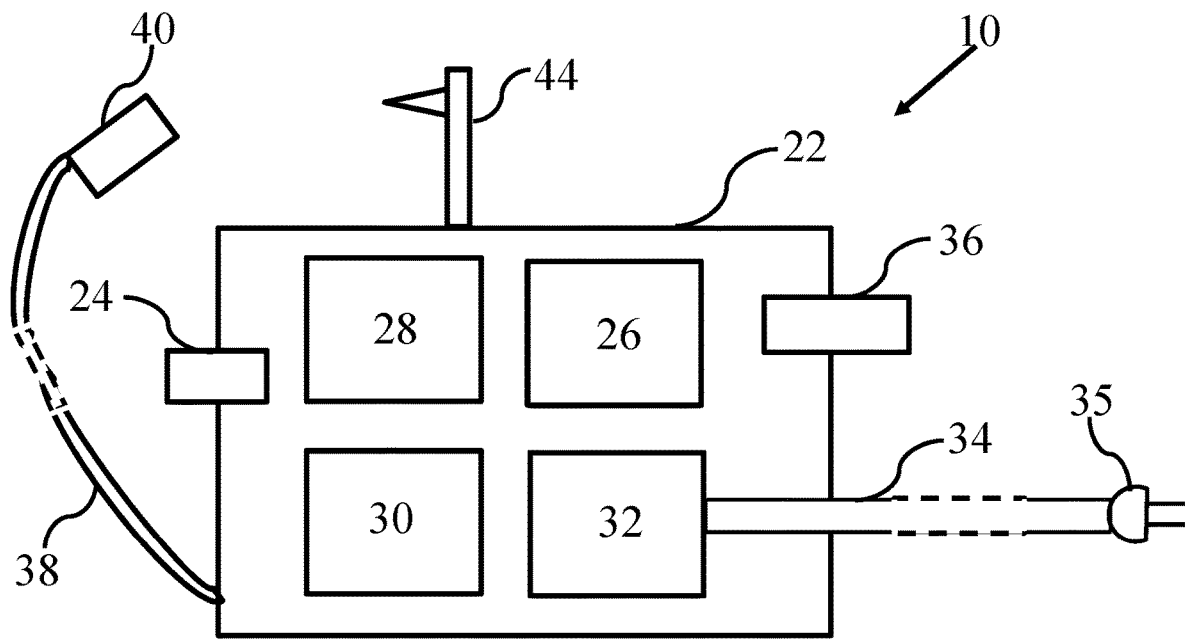
FIG. 2C is a schematic diagram showing elements of an exemplary device as disclosed herein, including a housing with an ON/OFF switch and containing a pressure source connected to a cuff configured to constrict a digit, the device including a lancing device, a timer, a signal source, a power supply connected to a power cable, and an (optional) link to a foot pedal (interrupt switch). In embodiments, the cuff may include a warming element (not shown in the figure).

FIG. 2C is a schematic diagram showing elements of an exemplary device 10 as disclosed herein, including a housing 22 with an ON/OFF switch 24 and containing a pressure source 26 connected via a conduit 38 to a cuff 40 configured to constrict a digit, the device including a lancing device 44, a timer 28, a signal source 30, a power supply 32 connected to a power cable 34, and an (optional) link to a foot pedal (interrupt switch) 36. In embodiments, the cuff 40 may include a warming element (not shown in the figure). A conduit 38 connects cuff 40 to the pressure source 26.

Figure 2D:
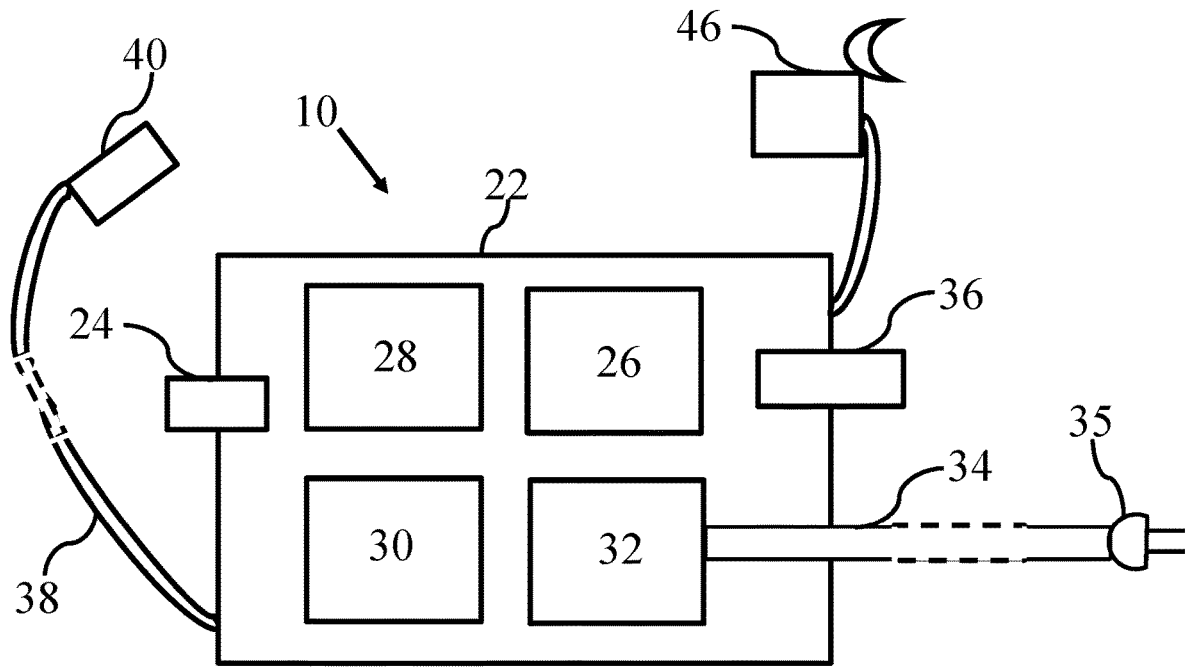
FIG. 2D is a schematic diagram showing elements of an exemplary device as disclosed herein, including a housing with an ON/OFF switch and containing a pressure source connected to a cuff configured to constrict a digit, a timer, a signal source, a power supply connected to a power cable, a communication element, and an (optional) link to a foot pedal (interrupt switch). In embodiments, the cuff may include a warming element (not shown in the figure).

FIG. 2D is a schematic diagram showing elements of an exemplary device 10 as disclosed herein, including a housing 22 with an ON/OFF switch 24 and containing a pressure source 26 connected via a conduit 38 to a cuff 40 configured to constrict a digit, a timer 28, a signal source 30, a power supply 32 connected to a power cable 34, a communication element 46, and an (optional) link to a foot pedal (interrupt switch) 36. In embodiments, the cuff 40 may include a warming element (not shown in the figure). A conduit 38 connects cuff 40 to the pressure source 26.

Figure 2E:
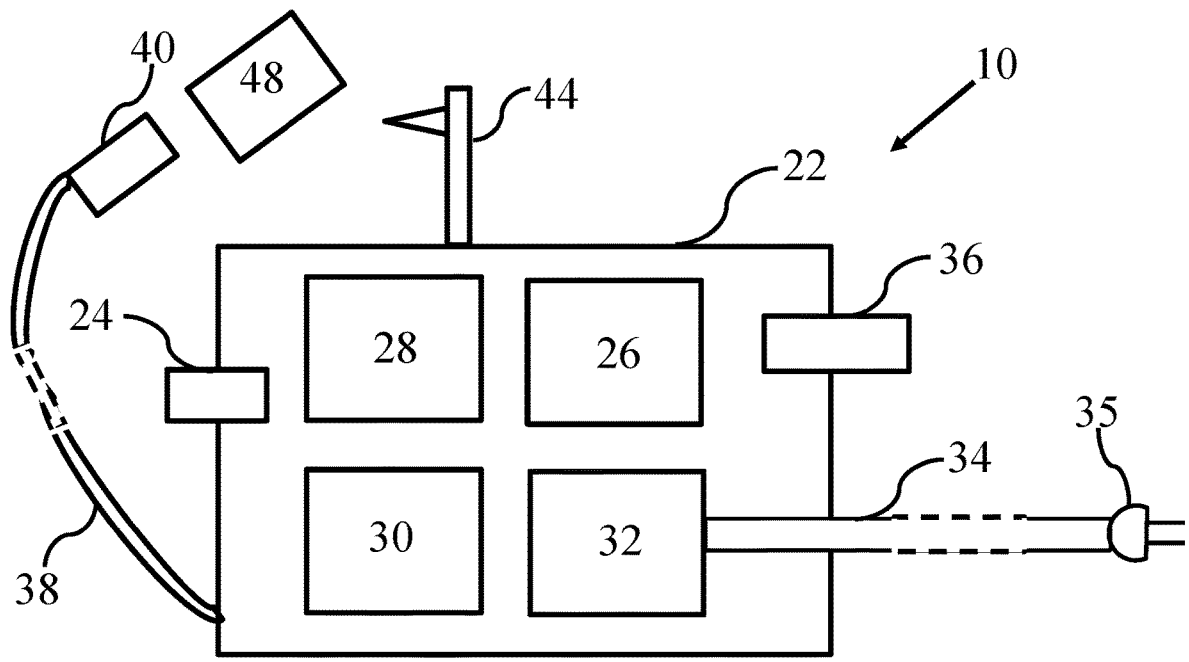
FIG. 2E is a schematic diagram showing elements of an exemplary device as disclosed herein, including a housing with an ON/OFF switch and containing a pressure source connected to a cuff configured to constrict a digit, a timer, a signal source, a lancing device, a sample collection element, a power supply connected to a power cable, and an (optional) link to a foot pedal (interrupt switch). In embodiments, the cuff may include a warming element (not shown in the figure).

FIG. 2E is a schematic diagram showing elements of an exemplary device 10 as disclosed herein, including a housing 22 with an ON/OFF switch 24 and containing a pressure source 26 connected to a cuff 40 configured to constrict a digit by a conduit 38, a timer 28, a signal source 30, a lancing device 44, a sample collection element 48, a power supply 32 connected to a power cable 34, and an (optional) link to a foot pedal (interrupt switch) 36. In embodiments, the cuff 40 may include a warming element (not shown in the figure). A conduit 38 connects cuff 40 to the pressure source 26.

Embodiments of devices as disclosed herein may include an ON/OFF switch (e.g., an ON/OFF switch 24 as shown in the figures). In embodiments, separate switches may individually perform ON and OFF functions independently of each other. In embodiments, further switches may be included in devices as disclosed herein.

A cuff (e.g., a cuff 40 as shown in the figures) is configured to be placed on or around a digit (e.g., a finger or toe) of a subject effective to compress a portion of the digit to constrict blood flow, effectively limiting blood flow out of the portion of the digit that is distal to the cuff. (As used herein, "distal" refers to locations on a digit farther away from the base of the digit, while "proximal" refers to locations on a digit closer to the base of the digit, where the base of a digit is the palm of the hand for a finger, and is the region near the ball or arch of the foot for a toe.) In embodiments, a cuff (when in place) may completely encircle a digit. When properly placed for use as disclosed herein, a cuff leaves at least a distal portion of a digit uncovered and exposed so as to provide a skin surface suitable for lancing in order to provide a fingerstick blood sample. In embodiments, about 5-10 mm of skin surface of a digit may be left exposed to provide a skin surface suitable for lancing. In embodiments, about 5 mm of skin surface of a digit may be left exposed to provide a skin surface suitable for lancing. In embodiments, more than about 10 mm of skin surface of a digit may be left exposed to provide a skin surface suitable for lancing.

A cuff (e.g., a cuff 40 as shown in the figures) is configured to inflate effective to constrict a digit, such as a finger, on or around which the cuff is disposed. A pressure source may be any suitable pressure source. Pressure for inflating the cuff may be air (or other gas) pressure, or may be fluid pressure (e.g., water, oil, or other fluid), or other pressure. Pressure for inflating the cuff is supplied by a pressure source (e.g., a pressure source 26 as shown in the figures). Any suitable pressure source may be used to provide pressure for inflating a cuff. A pressure source may be an electric pump, such as a rotary pump, or may be a peristaltic pump, or may include a piston, or may include other means or elements for producing pressure. A pressure source may include a combination or variety of pumps and pump mechanisms. In embodiments, a pressure source may be or may include a container holding compressed gas (e.g., a tank of compressed gas, such as compressed nitrogen, carbon dioxide, or other gas). A pressure source may be operably connected to the cuff by, e.g., a conduit (e.g., a conduit 38 as shown in the figures). A conduit may be a flexible conduit. A conduit may be made with any material, or combination of materials, which is capable of enclosing gas or fluid without significant loss of pressure, effective to allow a pressure source to pressurize a cuff and to inflate the cuff.

In embodiments, a cuff (e.g., a cuff 40 as illustrated in the figures) may include a warming element (e.g., a warming element 42 as illustrated in the figures), or may have a warming element (e.g., a warming element 42 as illustrated in the figures) attached. A warming element may be any suitable warming element. For example, a warming element may be, or may include, a heating coil (e.g., an electric heating coil). In embodiments, a heating coil may be embedded in a cuff, or may be placed around an exterior portion of a cuff, or may be placed on an interior portion of a cuff, or may be attached to an interior portion of a cuff, or to an exterior portion of a cuff, or to a distal portion or end of a cuff, or to a proximal portion or end of a cuff. A warming mechanism may be configured to warm a digit to about 2° C. above normal skin temperature, or to about 3° C. above normal skin temperature, or to about 4° C. above normal skin temperature, or to about 5° C. above normal skin temperature, or to about 7° C. above normal skin temperature, or to about 9° C. above normal skin temperature, or to about 10° C. above normal skin temperature, or to about 12° C. above normal skin temperature, or higher. A warming mechanism may be controlled, effective that a user of the device may adjust the amount of warming provided by the warming mechanism. For example a warming mechanism may be adjustable so that a user of the device may adjust the temperature to which the skin of the digit is to be warmed. In embodiments, the warming mechanism is operably connected to the timing mechanism, effective that warming may be provided for a set period of time; in embodiments, such a set period of time may be controlled by a timer.

In embodiments, other warming elements may be used with, or in place of, a heating coil. For example, a warming element may be, or may include, a chemical heating element (e.g., a chemical compound or material which provides heat, such as, for example, a super-saturated solution of sodium acetate). In embodiments, a warming element may be, or may include, a tube or conduit for carrying heated oil or other heated liquid to the cuff. Such warming elements may be embedded in a cuff, or may be placed around an exterior portion of a cuff, or may be placed on an interior portion of a cuff, or may be attached to an interior, or an exterior, or a distal, or a proximal portion of a cuff.

In embodiments, a timer (e.g., a timer 28 as illustrated in the figures) may include any suitable timing element or timing circuit effective to determine a period of time, or to measure a period of time, or to determine or measure a duration, or to provide a frequency (e.g., to provide a sequence of signals or waveforms at a desired frequency). A timer may be any suitable timer or timing element.

In embodiments, a signal source (e.g., a signal source 30 as illustrated in the figures) may be any suitable signal source or signaling element, and may produce any suitable signal. In embodiments, a signal source may provide an audible signal. In embodiments, a signal may be, or may include, an audible signal, where an audible signal is a signal that may be heard by a person with normal hearing. In embodiments, an audible signal may be a beep, or a click, or a chirp, or a tone, or a combination of tones, or a siren, or other sound. In embodiments, a signal source may provide a visible signal. In embodiments, a signal may be, or may include, a visible signal, where a visible signal is a signal that may be seen by a person with normal vision. In embodiments, a visible signal may be a light signal of any color, and may be a brief flash of light, or may be a flashing light (e.g., alternating illumination and extinction (or diminution) of a light signal), or may be a sustained light signal. In embodiments, a signal may be, or may include, a tactile signal, where a tactile signal is a signal that may be felt by a person with normal touch or somatosensory sensitivity. In embodiments, a tactile signal may be a contact signal (in which, e.g., a signal element normally not in contact with a technician is moved into place effective to contact the technician, or a signal element normally in contact with a technician is moved across or in relation to the technician so as to be felt by the technician); may be a pressure signal (in which, e.g., the contact pressure of a signal element normally in contact with a technician is altered by an increase in pressure or a decrease in pressure); or may be a vibration signal, in which a vibration produced by the signal source may be felt by the technician.

In embodiments, a power supply (e.g., a power supply 32 as illustrated in the figures) may be any suitable power supply, and may produce any suitable type and amount of power for use by the device. In embodiments, a power supply may be, e.g., an electric power supply. In embodiments, a power supply may be, e.g., an alternating current electric power supply, suitable for use with standard wall sockets. In embodiments, a power supply may be, or may include, e.g., a direct current electric power supply, suitable for use with standard batteries, or rechargeable batteries, or other electrical power source that does not require continuous connection to a wall socket during use.

In embodiments, an interrupt switch may be any interrupt switch effective to provide an interrupt command effective to temporarily pause application of pressure to the cuff, or effective to temporarily release pressure in the cuff. For example, an interrupt switch may be a foot pedal which, when stepped on, provides an electrical signal effective to interrupt application of pressure to the cuff.

In embodiments, a lancing device (e.g., a lancing device 44 as illustrated in the figures) may be any suitable lancing device or lancing element effective to lance a digit to provide a fingerstick wound for collection of a fingerstick blood sample. A lancing device may include a blade (e.g., a lancet) or a needle, or other sharp surface or sharp element configured to provide a small wound in the skin of a subject for releasing drops of blood.

A sample collection device or element (e.g., a sample collection element 48 as illustrated in the figures) may be any device or element configured to collect small amounts of blood. In embodiments, a sample collection device or element is configured to collect a fingerstick blood sample. In embodiments, a sample collection device may be automatic sample collection device. An automatic sample collection device may be any suitable automatic device which may collect a fingerstick sample from a subject. In embodiments, a sample collection device may be configured to work in conjunction with a lancing device as disclosed herein.

In embodiments, a communication link or communication element (e.g., a communication link 46 as illustrated in the figures) may be any suitable communication link or communication element. In embodiments, a communication link may be effective to communicate device status information from a device as disclosed herein to an external device, or to a laboratory, or to a network. In embodiments, a communication link may be effective to communicate device performance information from a device as disclosed herein to an external device, or to a laboratory, or to a network. In embodiments, a communication link may be effective to communicate device error or failure information from a device as disclosed herein to an external device, or to a laboratory, or to a network. In embodiments, a communication link may be effective to communicate data, such as raw data, from a device as disclosed herein to an external device, or to a laboratory, or to a network. In embodiments, a communication link may be effective to communicate raw data from a device as disclosed herein to a laboratory for performing sample analysis. In embodiments, a communication link may be effective to communicate data, such as image data, from a device as disclosed herein to an external device, or to a laboratory, or to a network. In embodiments, a communication link may be effective to communicate image data, from a device as disclosed herein to a laboratory for performing sample analysis. In embodiments, a communication link may be effective to communicate data, such as data from analysis of a sample, from a device as disclosed herein to an external device, or to a laboratory, or to a network. In embodiments, a communication link may be effective to communicate data from analysis of a sample from a device as disclosed herein to a laboratory for performing sample analysis.

Figure 3A:
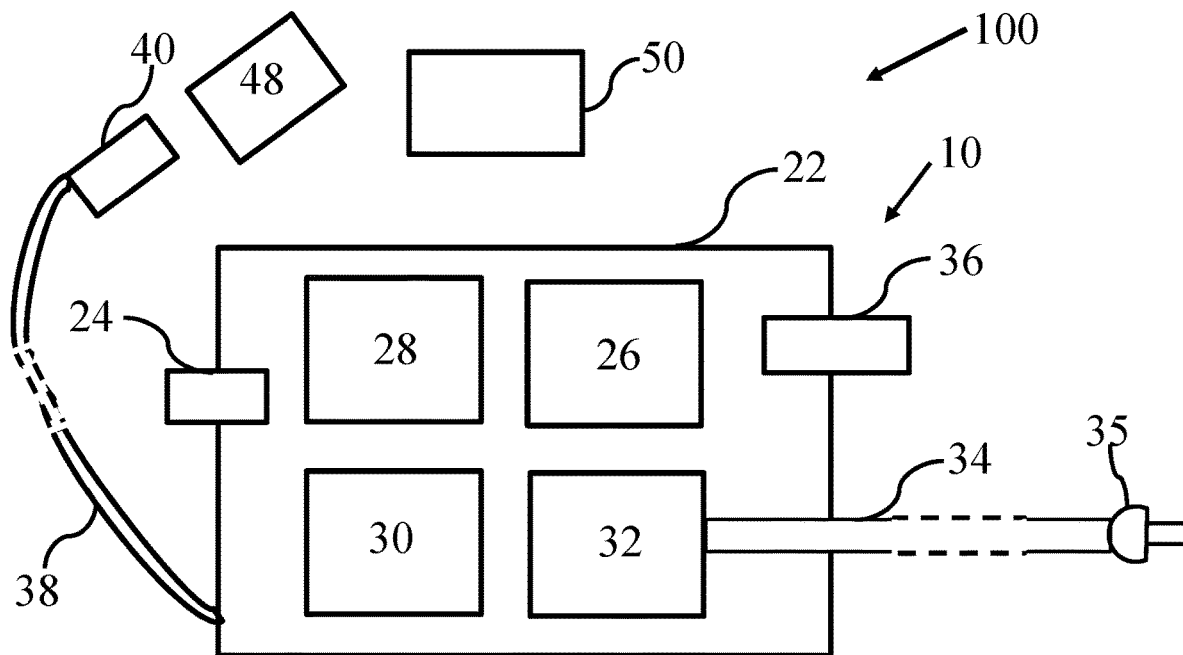
FIG. 3A is a schematic diagram showing elements of an exemplary system including a device as shown in FIGS. 1 and 2A-2E, including a housing with an ON/OFF switch and containing a pressure source connected to a cuff configured to constrict a digit, a timer, a signal source, a sample collection element, a power supply connected to a power cable, and an (optional) link to a foot pedal (interrupt switch). In embodiments, the cuff may include a warming element (not shown in the figure). In addition to the device within and associated with the housing, the system includes an automated sample analysis device.

FIG. 3A is a schematic diagram showing elements of an exemplary system 100 including a device 10 as shown in FIGS. 1 and 2B-2E, the device 10 including a housing 22 with an ON/OFF switch 24 and containing a pressure source 26 connected via a conduit 38 to a cuff 40 configured to constrict a digit, a timer 28, a signal source 30, a sample collection element 48, a power supply 32 connected to a power cable 32, and an (optional) link to a foot pedal (interrupt switch) 36. In embodiments, the cuff 40 may include a warming element (not shown in the figure). In addition to the device 10 within and associated with the housing 22, the system 100 includes an automatic sample analysis device 50. A conduit 38 connects cuff 40 to the pressure source 26.

Figure 3B:
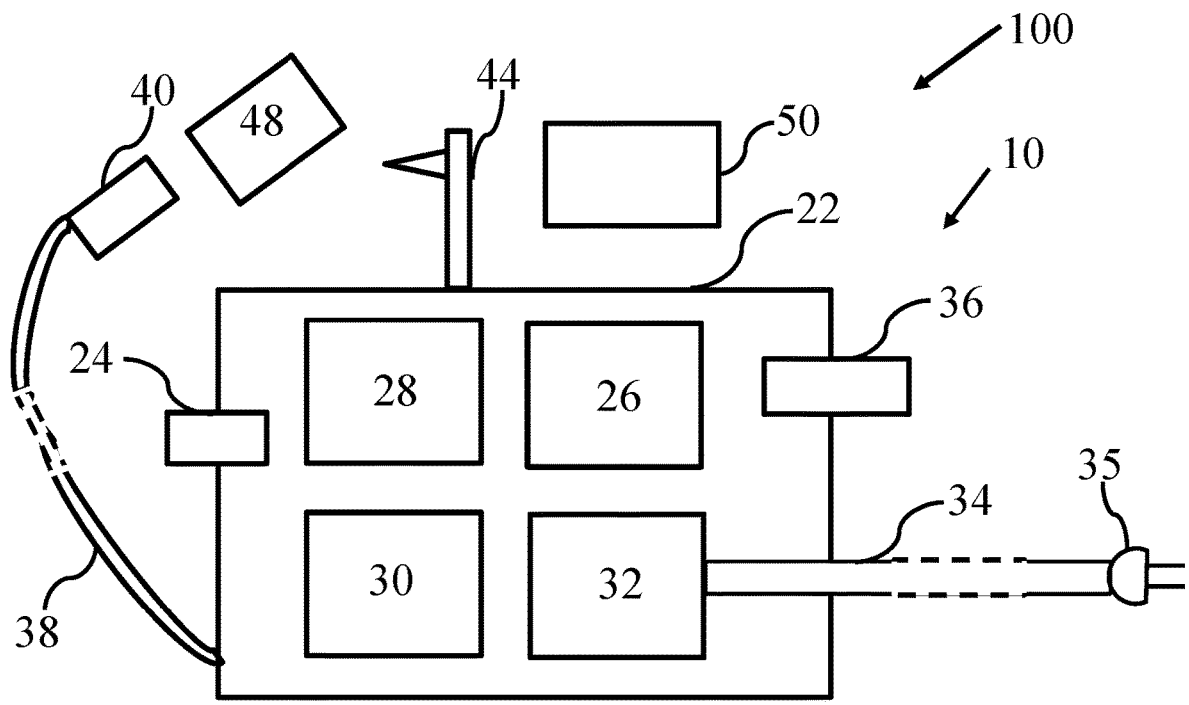
FIG. 3B is a schematic diagram showing elements of an exemplary system including a device as disclosed herein, the device including a housing with an ON/OFF switch and containing a pressure source connected to a cuff configured to constrict a digit, a timer, a signal source, a lancing device, a sample collection element, a power supply connected to a power cable, and an (optional) link to a foot pedal (interrupt switch). In embodiments, the cuff may include a warming element (not shown in the figure). In addition to the device within and associated with the housing, the system includes an automated sample analysis device.

FIG. 3B is a schematic diagram showing elements of an exemplary system 100 including a device 10 as disclosed herein, the device 10 including a housing 22 with an ON/OFF switch 24 and containing a pressure source 26 connected via a conduit 38 to a cuff 40 configured to constrict a digit, a timer 28, a signal source 30, a lancing device 44, a sample collection element 48, a power supply 32 connected to a power cable 34, and an (optional) link to a foot pedal (interrupt switch) 36. In embodiments, the cuff 40 may include a warming element (not shown in the figure). In addition to the device 10 within and associated with the housing, the system 100 includes an automatic sample analysis device 50. A conduit 38 connects cuff 40 to the pressure source 26.

An automatic sample analysis device 50 may be any suitable automatic sample analysis device which may be used to analyze, or to aid in the analysis of, a fingerstick sample collected from a subject. An automatic sample analysis device 50 may be configured to detect the presence of an analyte in a blood sample. An automatic sample analysis device 50 may be configured to measure the amount of an analyte in a blood sample. An automatic sample analysis device 50 may be configured to measure a property of a blood sample. In embodiments, a property of a blood sample may be, for example, the pH of a blood sample, the coagulation time of a blood sample, the hematocrit of a blood sample, the amount or percentage of blood oxygenation of a blood sample, and other properties. Exemplary automatic sample analysis devices are described, for example, in U.S. Pat. Nos. 8,380,541; 8,840,838; 8,435,738; 8,475,739; and U.S. patent application Ser. No. 14/183,503 filed Feb. 18, 2014, the entire contents of which patents and patent applications are hereby incorporated by reference in their entireties.

Methods

In embodiments, a method for collecting blood from a digit comprises at least partially encircling a human digit with a cuff of a device as disclosed herein; inflating said cuff effective to apply pressure to said digit; lancing said digit effective to puncture the skin of the digit and to allow blood to flow out of the digit; and collecting of at least a portion of said blood flowing out of the digit. In embodiments of methods for collecting blood from a digit as disclosed herein, inflation of the cuff is inflation to a maximum pressure of about 300 mm of mercury of pressure. In embodiments, a method for collecting blood from a digit, collecting of at least a portion of said blood flowing out of the digit comprises beginning collection of at least a portion of said blood flowing out of the digit; and ending collection of blood flowing out of said digit pursuant to a signal from said device. In embodiments, a method for collecting blood from a digit as disclosed herein comprises use of a device as disclosed herein, wherein the device comprises a timing mechanism configured to determine a period of time, and wherein said period of time is a desired period of time for collecting a fingerstick blood sample from said digit. In embodiments, a method for collecting blood from a digit as disclosed herein further comprise providing a signal at the end of such a period of time. In embodiments, such a period of time is at least about one minute in duration. In embodiments, such a period of time is 60 seconds in duration. In embodiments, a method for collecting blood from a digit as disclosed herein further comprise providing a signal at the beginning of said period of time. In embodiments, a method for collecting blood from a digit as disclosed herein further comprise ending inflation of said cuff at the end of said period of time. In embodiments of methods for collecting blood from a digit as disclosed herein, the signal comprises a signal selected from an audible signal, a visual signal, and a tactile signal. In embodiments of methods for collecting blood from a digit as disclosed herein, the signal comprises an electronic, hydraulic, or mechanical signal effective to end the collection of blood flowing out of said digit. In embodiments of methods for collecting blood from a digit as disclosed herein, the signal comprises an electronic, hydraulic, or mechanical signal operably connected to a sample collection mechanism effective to end the collection of blood flowing out of said digit. In embodiments, a device as disclosed herein comprises a sample collection mechanism that comprises, or is operably connected to, an electronic, hydraulic, or mechanical mechanism or element that is configured to provide a signal to end the collection of blood flowing out of a digit, or is configured to directly end the collection of blood flowing out of a digit. In embodiments, a system as disclosed herein comprises a device comprising a cuff as disclosed herein, the system further comprising a sample collection device that comprises, or is operably connected to, an electronic, hydraulic, or mechanical mechanism or element that is configured to provide a signal to end the collection of blood flowing out of a digit, or is configured to directly end the collection of blood flowing out of a digit.

In embodiments of methods for collecting blood from a digit as disclosed herein, the methods further comprise warming the digit. In embodiments of methods for collecting blood from a digit as disclosed herein, the cuff comprises a warming mechanism configured to warm a digit disposed within said cuff, and said warming is effected at least in part by said warming.

In embodiments of methods for collecting blood from a digit as disclosed herein, the device comprises a lancing mechanism configured to puncture a digit effective to make a wound or incision suitable for providing blood for sample collection, said cuff at least partially encircling a human digit, the method comprising lancing said digit with said lancing mechanism. In embodiments, such lancing is performed without contacting the cuff. In embodiments, such lancing is performed without puncturing the cuff. In embodiments, such lancing is automatically performed by a device. In embodiments, such lancing is automatically performed by a device, where that device is an automatic sample collection device. In embodiments, such lancing is automatically performed by a device, where that device is an automated sample collection device connected with, or part of, an automated sample analysis device.

In embodiments of methods for collecting blood from a digit as disclosed herein, the device comprises an automated sample collection device, and said method comprises automatically collecting the blood sample. In embodiments of methods for collecting blood from a digit as disclosed herein, the device comprises an automated sample collection device, and said method comprises diluting the blood sample. In embodiments of methods for collecting blood from a digit as disclosed herein, the device comprises an automated sample collection device, and said method comprises processing the blood sample. In embodiments of methods for collecting blood from a digit as disclosed herein, the device comprises an automated sample collection device, and said method comprises analyzing said blood sample.

In embodiments, the methods disclosed herein utilize a device having features as disclosed herein, the methods comprising use of a first device, wherein the first device comprises a communication unit effective to transmit data regarding a blood sample, and the method comprises transmitting data regarding said blood sample to a second device. In embodiments, such data is raw data obtained from the blood sample. In embodiments, such data is raw data obtained from processing of the blood sample. In embodiments, such data is raw data obtained from processing the blood sample in an automated sample analysis device. In embodiments, such data is analysis data obtained from the blood sample. In embodiments, such data is analysis data obtained from analyzing the blood sample. In embodiments, such data is analysis data obtained from analyzing the blood sample in an automated sample analysis device.

The methods disclosed herein include methods in which a digit of a subject is contacted, or is encircled, or both, by a cuff of a device or system disclosed herein. In embodiments of the methods disclosed herein, a digit of a subject is contacted, or is encircled, or both, by a cuff of a device or system disclosed herein and pressure is applied to at least a portion of that digit, or at least a portion of the digit is compressed, by the cuff as disclosed herein. In embodiments of the methods disclosed herein, a digit of a subject is lanced (punctured or otherwise wounded, effective to provide a passage for the flow of that subject's blood out of that digit); that digit is contacted, or is encircled, or both, by a cuff of a device or system disclosed herein; and pressure is applied to at least a portion of that digit, or at least a portion of the digit is compressed, by the element of a device or system disclosed herein, while blood flows from the lanced digit of the subject.

In embodiments of the methods disclosed herein, a digit of a subject is punctured, incised, or otherwise wounded, effective to provide a passage for the flow of that subject's blood out of that digit; a pulse of pressure is applied to that digit, by a cuff of a device or system disclosed herein effective that pressure or compression is applied to at least a portion of that digit, by the cuff, effective to allow collection of blood in the digit from which a fingerstick sample of blood is collected. In embodiments, the pulse of pressure is a constant pulse of pressure, and may be maintained during all or during part of the period of blood collection.

In embodiments of the methods disclosed herein, a digit of a subject is punctured, incised, or otherwise wounded, effective to provide a passage for the flow of that subject's blood out of that digit; that digit is contacted, or is encircled, or both, by a cuff of a device or system disclosed herein; and pressure is applied to at least a portion of that digit, or at least a portion of the digit is compressed, for a plurality of periods of time, wherein said plurality of periods of time may be separated by a time period during which compression or pressure is not applied to the digit, by the element of a device or system disclosed herein, while blood flows from the digit of the subject. In embodiments of the methods disclosed herein, a digit of a subject is punctured or otherwise wounded, effective to provide a passage for the flow of that subject's blood out of that digit; that digit is contacted, or is encircled, or both, by an element of a device or system disclosed herein; and pressure is applied to at least a portion of that digit, or at least a portion of the digit is compressed, for a plurality of periods of time, wherein said plurality of periods of time may be separated by a time period during which compression or pressure is not applied to the digit, by the element of a device or system disclosed herein, effective to express blood from the digit of the subject. Thus, in embodiments, the pulse of pressure is cycled, so that pulses of pressure to the digit are applied, and pressure is released, in a cyclic manner; such pulse cycling may be maintained during all or during part of the period of blood collection. In embodiments, such pulse cycling may be regular in its application (i.e., each period of cuff inflation is of substantially the same duration as the other periods of cuff inflation, and each period of cuff deflation is of substantially the same duration as the other periods of cuff deflation). In embodiments, such pulse cycling may be irregular in its application (i.e., a period of cuff inflation may be of different duration than other periods of cuff inflation, and a period of cuff deflation may be of different duration than other periods of cuff deflation).

In embodiments of the methods disclosed herein, a digit of a subject is punctured or otherwise wounded, effective to provide a passage for the flow of that subject's blood out of that digit, and pressure may be repeatedly applied to at least a portion of that digit at a defined frequency of application of compression or pressure; in embodiments, periods of time during which compression or pressure is applied may be separated by time periods during which compression or pressure is not applied to the digit. In some embodiments, the frequency of application of pressure or compression to a digit may be unvarying; and, in other embodiments, the frequency of application of pressure or compression to a digit may vary. In some embodiments, the duration of time periods during which compression or pressure is not applied to the digit may be unvarying; and, in other embodiments, the duration of time periods during which compression or pressure is not applied to the digit may vary. In such embodiments, the repeated contact with the digit, or repeated application of pressure to the digit, may be performed while blood flows from the digit of the subject. In such embodiments, the repeated contact with, or repeated application of pressure to, the digit may be effective to increase the amount of blood collected from the digit of the subject, or to decrease the amount of time required to collect a desired amount of blood, as compared to such fingerstick blood sample collection by other methods or with other devices.

In embodiments of the methods disclosed herein, the time period of contact with the digit, or of application of pressure to the digit, is a time period that is less than the time required for the blood flow from the digit to slow or stop. In embodiments of the methods disclosed herein, the time period of repeated contact with the digit, or of repeated application of pressure to the digit, is a time period that is less than the time required for the blood flow from the digit to slow or stop. In embodiments of the methods disclosed herein, the time period of contact with the digit, or of application of pressure to the digit, is a time period that is less than the time required for the blood flowing from the digit to coagulate. In embodiments of the methods disclosed herein, the time period of cyclic pressure pulses applied to the digit, or of repeated application of pressure to the digit, is a time period that is less than the time required for the blood flowing from the digit to coagulate. In embodiments, such a time period of cyclic application of pressure pulses may be less than about 100 seconds from the time of lancing; or may be less than about 90 seconds; or may be less than about 80 seconds; or may be less than about 70 seconds; or may be less than about 60 seconds.

In embodiments of the methods disclosed herein, the time period of contact with the digit, or of application of pressure to the digit, is a time period that is less than the time required for interstitial fluid in the digit to significantly contaminate the blood flowing from the digit. In embodiments of the methods disclosed herein, the time period of repeated contact with the digit, or of repeated application of pressure to the digit, is a time period that is less than the time required for interstitial fluid in the digit to significantly contaminate the blood flowing from the digit. In embodiments of the methods disclosed herein, significant contamination of the blood is contamination by greater than 20% by volume interstitial fluid; or is contamination by greater than 15% by volume interstitial fluid; or is contamination by greater than 10% by volume interstitial fluid; or is contamination by greater than 5% by volume interstitial fluid; or is contamination by greater than 4% by volume interstitial fluid; or is contamination by greater than 3% by volume interstitial fluid; or is contamination by greater than 2% by volume interstitial fluid; or is contamination by greater than 1% by volume interstitial fluid. In embodiments, the time required for interstitial fluid in the digit to significantly contaminate the blood flowing from a digit may be greater than about 60 seconds from the time of lancing; or may be greater than about 70 seconds; or may be greater than about 80 seconds; or may be greater than about 90 seconds; or may be greater than about 100 seconds.

In embodiments of the methods disclosed herein, such time periods are times less than the time required for significant degradation in the quality of the sample, are times less than time required for significant degradation of the integrity of the sample, and are times less than the time required for loss of integrity of the sample. Indications of the degradation in, or loss of, integrity of a sample include hemolysis of cells in the sample, coagulation of the sample, and contamination of the blood sample by interstitial fluid.

In such embodiments, the repeated contact with, or repeated application of pressure to, the digit may be effective to improve the collection of blood from the digit of the subject. In such embodiments, the pulse applied by a device or system disclosed herein provides repeated contact with, or repeated application of pressure to, the digit, and may be effective to express blood from the digit of the subject.

Methods for collecting blood from a digit as disclosed herein may be practiced or performed at any suitable location. In embodiments, such a suitable location may include a clinical laboratory, a hospital, a doctor's office, a clinic, a retail store, a school, a community center, a library, and combinations thereof. In embodiments, devices for collecting blood from a digit as disclosed herein are located at a point-of-care location. In embodiments, such a point-of-care location is selected from the group of point-of-care locations consisting of a hospital, a doctor's office, a clinic, and combinations thereof.

Devices and systems for automated fingerstick blood collection as disclosed herein may provide automated pressure application to a digit of a subject; such pressure application may be sustained during a continuous period of time. For example, a cuff 40 disposed on a digit may be inflated, and inflation maintained for a period of time (e.g., about 3 seconds, or about 5 seconds, or longer) prior to lancing the digit. A period of maintained pressure prior to lancing may be termed an "initial period" of pressure application. In embodiments, pressure is applied to the digit (e.g., the cuff is inflated) for about 3 seconds, and a signal is provided to indicate that lancing of the digit is to be performed; such a period of time during which lancing is to be performed may be termed a "lancing period." Application of pressure to the digit may be maintained during this lancing period; for example, cuff pressure may be maintained for about 5 seconds following the initial (e.g., 3 second) period of pressure application. In embodiments, pulsing (e.g., cyclic application and relief of cuff pressure) may begin immediately following the lancing period. Such maintained inflation may continue to be maintained for a period of time following lancing of the digit, and may be maintained while blood is collected from that digit.

Figure 4A:
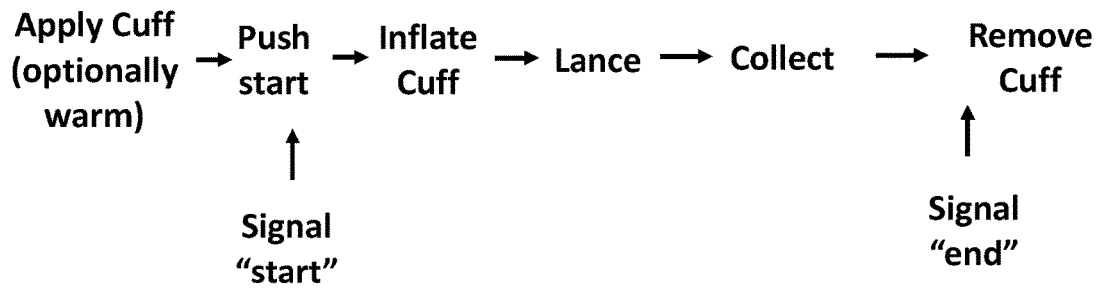
FIG. 4A is a schematic diagram showing methods which may be performed using the devices and systems disclosed herein, effective to automate much of the process of obtaining blood from a subject by fingerstick. Blood may be collected by fingerstick following application of pressure to a digit via a cuff placed around a digit, and lancing of the digit. In embodiments, a digit may be warmed prior to lancing. In embodiments, blood may be collected by manual fingerstick; for example, lancing may be manually performed, blood collection may be manually collected, or both lancing and collection may be performed manually. In embodiments, lancing may be automatically performed, blood collection may be automatically collected, or both lancing and collection may be performed automatically. The horizontal line beginning above the "Inflate Cuff" step and ending above the "Signal End" step indicates the time period during which the cuff is inflated; the dashed portion of that line indicates that (optionally) the cuff may be deflated before the collection period has ended (i.e., while collection continues).
Figure 4B:
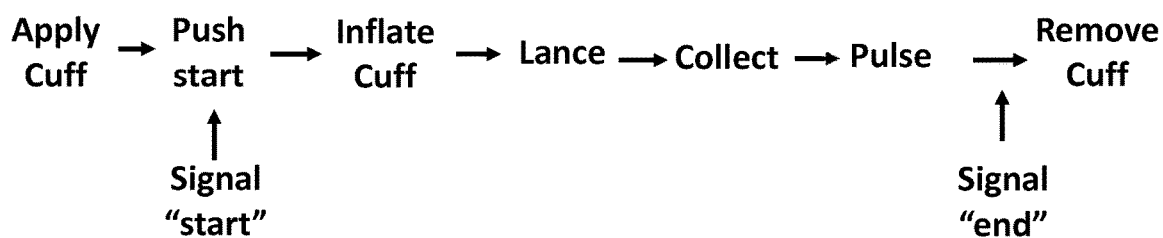
FIG. 4B is a schematic diagram showing methods which may be performed using the devices and systems disclosed herein, effective to automate much of the process of obtaining blood from a subject by fingerstick. Blood may be collected by fingerstick following application of pressure to a digit via a cuff placed around a digit, lancing of the digit, and pulsing the pressure applied by the cuff. In embodiments, blood may be collected by manual fingerstick; for example, lancing may be manually performed, blood collection may be manually collected, or both lancing and collection may be performed manually. In embodiments, lancing may be automatically performed, blood collection may be automatically collected, or both lancing and collection may be performed automatically. The horizontal line beginning above the "Inflate Cuff" step and ending above the "Signal End" step indicates the time period during which the cuff is inflated; the diagonal lines indicate the time period during which pulses of inflation may be applied (during which the cuff is repeatedly inflated and at least partially deflated between periods of inflation). Such pulsing may begin at any suitable time after collection of blood has begun, and may begin at the same time as blood collection is begun.

In embodiments, such inflation may continue to be maintained for part, or for all, of the period of time following lancing while blood is collected from that digit. Application of pressure is indicated in FIGS. 4A to 4B by a horizontal line above the text and arrows of these figures. The "Inflate Cuff" step shown in FIGS. 4A to 4D indicates that pressure is applied to the digit (e.g., the cuff is inflated); such inflation of the cuff may be maintained from that time forward until the "Remove Cuff" step. The dashed portion of the horizontal line of FIG. 4A indicates that pressure may optionally be relieved during part or all of the collection period; typically, when relieved in this way, pressure application (e.g., cuff inflation) may be relieved some time after collection of blood has begun. For example, in embodiments, cuff inflation may be relieved about 30 seconds, or about 40 seconds, or about 50 seconds after collection of blood from a lanced digit has begun.

Figure 4C:
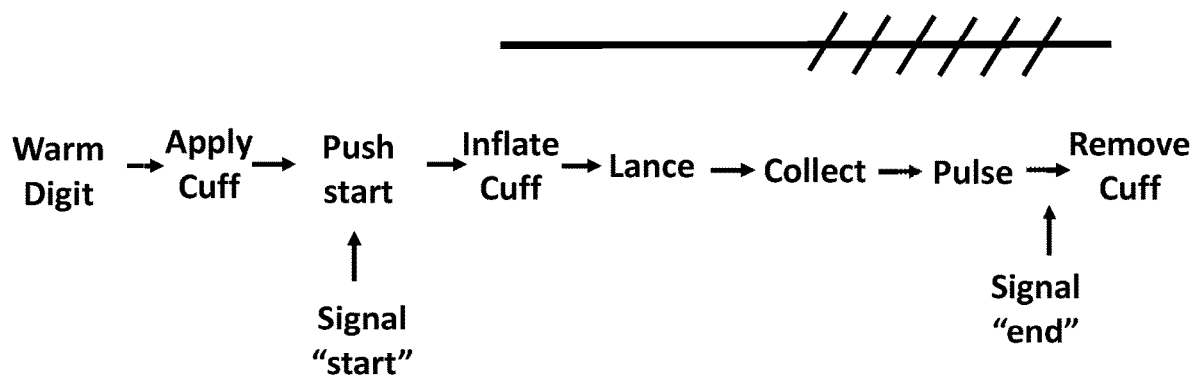
FIG. 4C is a schematic diagram showing methods which may be performed using the devices and systems disclosed herein, effective to automate much of the process of obtaining blood from a subject by fingerstick. A digit may be warmed, and blood may be collected by fingerstick following application of pressure to a digit via a cuff placed around a digit, lancing of the digit, with pulsing the pressure applied by the cuff. The horizontal line beginning above the "Inflate Cuff" step and ending above the "Signal End" step indicates the time period during which the cuff is inflated; the diagonal lines indicate the time period during which pulses of inflation may be applied (during which the cuff is repeatedly inflated and at least partially deflated between periods of inflation). Such pulsing may begin at any suitable time after collection of blood has begun, and may begin at the same time as blood collection is begun.
Figure 4D:
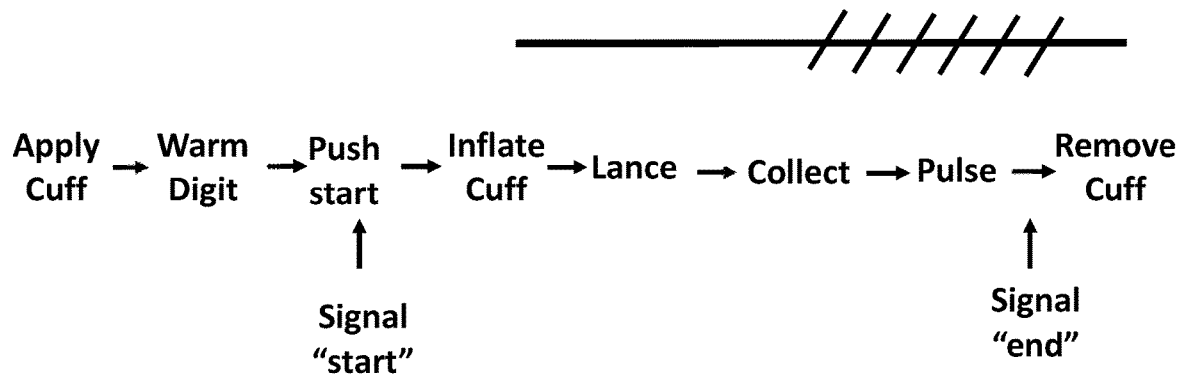
FIG. 4D is a schematic diagram showing methods which may be performed using the devices and systems disclosed herein, effective to automate much of the process of obtaining blood from a subject by fingerstick. Blood may be collected by fingerstick following application of pressure to a digit via a cuff placed around a digit, warming the digit, lancing of the digit, with pulsing the pressure applied by the cuff. Warming may be provided by a cuff having a warming element, for example, as shown in FIG. 2B. The horizontal line beginning above the "Inflate Cuff" step and ending above the "Signal End" step indicates the time period during which the cuff is inflated; the diagonal lines indicate the time period during which pulses of inflation may be applied (during which the cuff is repeatedly inflated and at least partially deflated between periods of inflation). Such pulsing may begin at any suitable time after collection of blood has begun, and may begin at the same time as blood collection is begun.

In addition, as shown in FIGS. 4B to 4D, such pressure application (e.g., cuff inflation) may be applied in a pulsatile manner, so that the digit experiences periods of pressure application separated by periods of relief of pressure (e.g., periods of cuff inflation separated by periods of cuff deflation). Thus, the "Pulse" step indicates that the cuff inflation begun with the "Inflate Cuff" step is modulated beginning with the "Pulse" step of FIG. 4B; pulsing the cuff may occur while collecting blood. Pulsing of pressure application is indicated by the diagonal lines above the steps labelled "Collect" and "Pulse" in FIGS. 4B, 4C, and 4D. As indicated by the methods disclosed in FIG. 4A, methods disclosed herein may be performed with maintained pressure application (which is begun as indicated in FIGS. 4A to 4D by the "Inflate Cuff" step, and which then may continue until the "Remove Cuff" step) and without a "pulse" step. The methods disclosed in FIGS. 4B to 4D include a "pulse" step indicating cyclic application of pressure to a digit (e.g., cyclic inflation of a cuff enclosing a digit). Such cyclic application of pressure may begin immediately following lancing of the digit and initiation of blood collection, or may begin at some later time following lancing of the digit and initiation of blood collection.

As shown in FIGS. 4A-4D, devices and systems for automated fingerstick blood collection as disclosed herein may provide automated pressure application to a digit of a subject (FIG. 4A); may provide automated cyclic pressure application to a digit of a subject (FIG. 4B); and may provide heat application and automated cyclic pressure application to a digit of a subject (FIGS. 4C and 4D). In embodiments, lancing of the digit may be performed manually; and in embodiments, lancing of the digit may automated.

In particular, FIG. 4A provides a schematic diagram of methods which automate much of the process of obtaining blood from a subject by fingerstick. Blood may be collected by fingerstick following application of pressure to a digit via a cuff placed around a digit, and lancing of the digit. The cuff is typically positioned effective to leave a portion, typically a distal portion, of the digit exposed and available for lancing. The application of pressure in a cuff around a digit is believed to constrict the digit, and to improve the collection of blood from a fingerstick, as compared to collection of fingerstick blood from a digit which is not constricted by a cuff or other means. It will be understood that a cuff may partially encircle, or may completely encircle, a portion of a digit, effective to constrict a portion of the digit when inflated. Such methods including application of pressure to a portion of a digit within a cuff, effective to constrict the digit, are disclosed herein.

FIGS. 4B-4D disclose that pressure application may be pulsed, i.e., pressure may be applied, released, and applied again, and may be repeatedly applied, released, and applied again. Where pressure is applied by a cuff, a pulse may include inflation of a cuff, followed by deflation of the cuff; and may be repeated cycles of inflation of a cuff, followed by deflation of the cuff. In embodiments, deflation may be partial deflation of a cuff. It will be understood that, in embodiments, pressure may be applied to a digit, and maintained during collection of blood; or may applied to a digit, and maintained for a portion of the time during collection of blood, and then pressure may be released for the duration of the collection time.

The application of pressure to a digit via a cuff placed around a digit is believed to impede or block blood flow out of the digit (while allowing some blood flow into the digit), allowing blood to pool in distal portions of the digit, providing greater amounts of blood readily available for collection from that digit following lancing. For example a cuff may be placed around a finger at a position spaced away from the fingertip, and typically closer to the base of the finger than the tip of the finger. Inflation of a cuff situated in that way prevents blood flow out of the digit tip, and prevents blood flow from the digit into the main part of the hand. It is believed that, while the cuff is inflated, blood collects in the portion of the finger that is closer to the finger tip than cuff. Lancing the finger, and collecting blood flowing out of the finger, provides blood for a fingerstick blood sample. It will be understood that, although the exemplary digit referred to in this discussion was a finger, a fingerstick blood sample may be obtained by the same or similar methods from a toe, or a heel, or an earlobe, or other body part or body surface.

In embodiments, a cuff may be inflated to an internal pressure of up to about 400 millimeters of mercury (mm Hg), where such a pressure is measured with respect to, and is in addition to, ambient atmospheric pressure (normal atmospheric pressure is typically about 760 mm Hg). Thus, as discussed herein, where an internal pressure is indicated, such an internal pressure is to be understood as referring to pressure that is in addition to ambient atmospheric pressure. In embodiments, a cuff may be inflated to an internal pressure of no more than about 400 mm Hg. In embodiments, a cuff may be inflated to an internal pressure of between about 200 mm Hg and about 400 mm Hg. In embodiments, a cuff may be inflated to an internal pressure of between about 250 mm Hg and about 350 mm Hg. In embodiments, a cuff may be inflated to an internal pressure of up to about 300 millimeters of mercury (mm Hg). In embodiments, a cuff may be inflated to an internal pressure of no more than about 300 mm Hg. In embodiments, a cuff may be inflated to an internal pressure of between about 200 mm Hg and about 300 mm Hg.

In embodiments, a cuff may be deflated, following inflation, to an internal pressure of less than about 200 mm Hg. In embodiments, a cuff may be deflated, following inflation, to an internal pressure of less than about 100 mm Hg. In embodiments, a cuff may be deflated, following inflation, to an internal pressure of about 0 mm Hg. In embodiments, a cuff may be deflated, following inflation, to an internal pressure of between about 100 mm Hg and about 200 mm Hg. In embodiments, a cuff may be deflated, following inflation, to an internal pressure of between about 0 mm Hg and about 100 mm Hg. In embodiments, a cuff may be deflated, following inflation, to an internal pressure of about 50 mm Hg or less. As indicated above, an internal pressure of about 0 mm Hg is an internal pressure that does not differ from ambient atmospheric pressure.

For example, pressure application may continue for the part or all of the duration of the period of time during which blood is collected from the lanced finger. The duration of the period of time during which blood is collected from the lanced finger may be about 20 seconds, or may be about 30 seconds, or may be about 40 seconds, or may be about 50 seconds, or may be about 60 seconds, or may be about 70 seconds, or may be about 80 seconds, or may be about 90 seconds. In embodiments, pressure application may continue for the entire duration of the period of time during which blood is collected from the lanced finger. In embodiments, pressure application may continue for less than the duration of the period of time during which blood is collected from the lanced finger; for example, pressure may be released following an initial period of time during which pressure is applied, while fingerstick blood may be collected both during and after application of pressure by the cuff. The duration of the period of time during which pressure is applied, prior to releasing pressure while blood is being collected from the lanced finger may be about 20 seconds, or may be about 30 seconds, or may be about 40 seconds, or may be about 50 seconds, or may be about 60 seconds, or may be about 70 seconds, or may be about 80 seconds, or may be about 90 seconds.

In embodiments, an automated device as disclosed herein may provide a signal indicating the beginning of the period of time during which blood is to be collected from the lanced finger. Such a signal is detectable by a technician operating a device as disclosed herein, or collecting a fingerstick sample of blood, or both. In embodiments, such a signal may be a signal may be detectable without interfering with the operation of a device as disclosed herein, or the collection of a fingerstick sample of blood, or both, by a technician. Such a signal may be an audible signal (i.e., a signal which may be heard by a technician collecting fingerstick blood sample from the digit, such as the onset of a tone, or beep, or other sound), a visible signal (i.e., a signal which may be seen by a technician collecting fingerstick blood sample from the digit, such as the onset of a light), may be a tactile signal (i.e., a signal which may be felt by a technician collecting fingerstick blood sample from the digit, such as a vibration), and may include combinations thereof. In embodiments in which the automated device collects fingerstick blood from a digit, the device may initiate such blood collection. In embodiments in which the automated device collects fingerstick blood from a digit, the device may provide a signal indicating the beginning of the period of time during which blood is to be collected from the lanced finger, and may initiate such blood collection.

In embodiments, an automated device as disclosed herein may provide a signal indicating the end of the period of time during which blood is to be collected from the lanced finger. Such a signal is detectable by a technician operating a device as disclosed herein, or collecting a fingerstick sample of blood, or both. In embodiments, such a signal may be a signal may be detectable without interfering with the operation of a device as disclosed herein, or the collection of a fingerstick sample of blood, or both, by a technician. Such a signal may be an audible signal (i.e., a signal which may be heard by a technician collecting fingerstick blood sample from the digit, such as the onset of a tone, or beep, or other sound), or a visible signal (i.e., a signal which may be seen by a technician collecting fingerstick blood sample from the digit, such as the onset of a light), or may be a tactile signal (i.e., a signal which may be felt by a technician collecting fingerstick blood sample from the digit, such as a vibration), or may include combinations thereof. In embodiments in which the automated device collects fingerstick blood from a digit, the device may stop such blood collection. In embodiments in which the automated device collects fingerstick blood from a digit, the device may provide a signal indicating the end of the period of time during which blood is to be collected from the lanced finger, and may stop such blood collection.

FIG. 4B is a schematic diagram showing processes provided by the devices and systems disclosed herein, effective to automate much of the process of obtaining blood from a subject by fingerstick. Blood may be collected by fingerstick following application of pressure to a digit via a cuff placed around a digit, lancing of the digit, and pulsing the pressure applied by the cuff. As used herein, "pulsing the pressure" refers to inflation of the cuff followed by deflation of the cuff, and, in embodiments of "pulsing the pressure", refers to repeated cycles of inflation of the cuff followed by deflation of the cuff. Deflation of a cuff during a pulse may be partial deflation (i.e., some residual amount of pressure remains within the cuff, where pressure is determined with respect to ambient atmospheric pressure) or may be complete deflation (substantially no pressure remains within the cuff). The cuff is typically positioned effective to leave a portion, typically a distal portion, of the digit exposed and available for lancing. It will be understood that a cuff may partially encircle, or may completely encircle, a portion of a digit, effective to constrict a portion of the digit when inflated.

In embodiments, a cuff may be pulsed (i.e., inflated and then deflated), where when inflated the cuff is inflated to an internal pressure between about 250 mm Hg and about 350 mm Hg, and when deflated the internal pressure of the cuff is reduced to about 200 mm Hg or less. In embodiments, a cuff may be pulsed, where when inflated the cuff is inflated to an internal pressure about 300 mm Hg, and when deflated the internal pressure of the cuff is reduced to about 100 mm Hg or less. In embodiments, a cuff may be pulsed, where when inflated the cuff is inflated to an internal pressure about 300 mm Hg, and when deflated the internal pressure of the cuff is reduced to about 50 mm Hg or less.

The pulsing of pressure in a cuff around a digit is believed to improve the collection of blood from a fingerstick, as compared to collection of fingerstick blood from a digit in a cuff which is not pulsed in a cyclic manner. Such methods including cyclic pulsing of pressure within a cuff, effective to constrict and to release constriction of a digit, are disclosed herein.

In particular, FIG. 4B provides a schematic diagram of methods which automate much of the process of obtaining blood from a subject by fingerstick. In the methods illustrated in FIG. 4B, fingerstick blood may be collected following a) application of pressure to a digit via a cuff placed around a digit, b) following lancing of the digit, and c) during cyclic application of pressure to a digit via a cuff placed around a digit. In these methods, a cuff is placed around a portion of a digit, leaving part of the digit exposed and available for lancing. Next, pressure is applied to the cuff, constricting the digit. The application of pressure to a digit via a cuff placed around a digit is believed to impede or block blood flow out of the digit, allowing blood to pool in distal portions of the digit, providing greater amounts of blood readily available for collection from that digit following lancing. Next, the digit is lanced, allowing blood to flow out of the digit and allowing collection of the fingerstick blood sample. Collection may begin at this time. The cuff is cyclicly inflated and deflated during collection of the fingerstick blood sample. The cyclic inflation and deflation of the cuff cyclicly constricts and diminishes (or releases) constriction of the digit during collection of the fingerstick blood sample. Reducing, or releasing, the pressure on the cuff may allow more blood to flow into the fingertip and to provide further blood for a fingerstick blood sample. The cycle of pressure application and release of pressure may be repeated once, twice, three times, four times, or more times. The cycle of pressure application and release of pressure may be repeated multiple times, and may continue for the duration of the period of time during which blood is collected from the lanced finger. It will be understood that, although the exemplary digit referred to in this discussion was a finger, a fingerstick blood sample may be obtained by the same or similar methods from a toe, or a heel, or an earlobe, or other body part or body surface.

For example, cyclic pressure application and release of pressure may be performed with one second of application of pressure followed by one second of release of pressure; and may be repeated once, twice, three times, four times, or more times. For example, a cycle of pressure application and release of pressure, in which pressure is applied for one second, and pressure is released for one second, may be 10 times, or may be repeated 20 times, or may be repeated 30 times, or may be repeated 40 times, or may be repeated 50 times, or may be repeated 60 times, or may be repeated 70 times, or may be repeated 80 times, or may be repeated 90 times, or more. Such a cycle may be repeated multiple times, and may continue for the duration of the period of time during which blood is collected from the lanced finger. In embodiments in which pressure is cyclicly applied to a digit by a cuff, the duration of the period of time during which blood is collected from the lanced finger may be 10 seconds, 20 seconds, 30 seconds, 40 seconds, 50 seconds, 60 seconds, 70 seconds, 80 seconds, 90 seconds, or more. In embodiments in which pressure is cyclicly applied to a digit by a cuff, the duration of the period of time during which blood is collected from the lanced finger may be about 50 seconds, or may be about 60 seconds, or may be about 70 seconds, or may be about 80 seconds, or may be about 90 seconds.

In embodiments, as discussed above, an automated device as disclosed herein may provide a signal indicating the beginning of the period of time during which blood is to be collected from the lanced finger. As discussed above, such a signal may be an audible signal, a visible signal, may be a tactile signal, and may include combinations thereof. In embodiments in which the automated device collects fingerstick blood from a digit, the device may initiate such blood collection. In embodiments in which the automated device collects fingerstick blood from a digit, the device may provide a signal indicating the beginning of the period of time during which blood is to be collected from the lanced finger, and may initiate such blood collection.

In embodiments, an automated device as disclosed herein may provide a signal indicating the end of the period of time during which blood is to be collected from the lanced finger. Such a signal may be an audible signal (i.e., a signal which may be heard by a technician collecting fingerstick blood sample from the digit, such as the onset of a tone, or beep, or other sound), or a visible signal (i.e., a signal which may be seen by a technician collecting fingerstick blood sample from the digit, such as the onset of a light), or may be a tactile signal (i.e., a signal which may be felt by a technician collecting fingerstick blood sample from the digit, such as a vibration). In embodiments in which the automated device collects fingerstick blood from a digit, the device may stop such blood collection. In embodiments in which the automated device collects fingerstick blood from a digit, the device may provide a signal indicating the end of the period of time during which blood is to be collected from the lanced finger, and may stop such blood collection.

FIGS. 4C and 4D are schematic diagrams showing processes provided by the devices and systems disclosed herein, effective to automate much of the process of obtaining blood from a subject by fingerstick. In embodiments, methods as illustrated in FIGS. 4C and 4D may include steps as indicated in FIG. 4B and further include warming a digit (e.g., warming a digit prior to application of a cuff to a digit, as shown in FIG. 4C; and warming a digit following application of a cuff to a digit, as shown in FIG. 4D); in such embodiments, blood may be collected by fingerstick following application of pressure to a digit via a cuff placed around a digit, warming the digit, and lancing of the digit. In embodiments further including pulsing pressure in a cuff as illustrated in FIGS. 4C and 4D, blood may be collected by fingerstick following application of pressure to a digit via a cuff placed around a digit, warming the digit, and lancing of the digit, and pulsing the pressure applied by the cuff. Thus, methods including steps as illustrated in FIGS. 4C and 4D include warming a digit, and include steps as indicated in FIGS. 4A and 4B, and as discussed above with regard to FIGS. 4A and 4B.

In embodiments, warming a digit may begin prior to inflating a cuff in which the digit is placed. In embodiments, a warming mechanism may be part of a cuff, effective to contact a digit when the cuff is placed on or around the digit. In embodiments, a warming mechanism may be within a cuff, effective to warm a digit when the cuff is placed on or around the digit. In embodiments, a warming mechanism may be disposed on an exterior surface of a cuff, effective to contact a digit for warming the digit when the cuff is placed on or around the digit. In embodiments, a warming mechanism may be connected to a part of a cuff, effective to contact a digit for warming the digit when the cuff is placed on or around the digit. In embodiments, warming a digit may begin prior to lancing the digit. In embodiments, warming a digit may begin prior to lancing the digit, and may cease prior to lancing the digit. In embodiments, warming a digit may begin prior to lancing the digit, and may continue following lancing the digit.

Embodiments of the automated fingerstick blood collection methods, devices, systems, and kits disclosed herein include a kit for fingerstick blood collection, comprising a device as disclosed herein and a sample collection vessel. In an embodiment, a kit for fingerstick blood collection comprises a device as disclosed herein, a sample collection vessel, and a disposable for use in sample collection. In embodiments, a disposable for use in sample collection may be a sterile swab (e.g., an alcohol swab), may be an absorbent pad (e.g., a cotton gauze pad for placement over a fingerstick wound), may be a bandage (e.g., a small self-adhesive bandage for placement over a fingerstick wound or over a gauze pad on a fingerstick wound), other disposables for use in a sample collection location (e.g., a clinical laboratory, a doctor's office, a clinic, a retail location, or other location in which a fingerstick sample may be obtained from a subject), and combinations thereof.

In embodiments, a device having features as disclosed herein is configured to provide automated finger-pressure cycling and to indicate a collection period (a "collection window") that is a fixed period of time. In embodiments, a device having features as disclosed herein is configured to provide automated finger-pressure cycling, to indicate a collection period (a "collection window") that is a fixed period of time, and includes a finger warmer. In embodiments, a device having features as disclosed herein is configured to provide automated finger-pressure cycling, to indicate a collection period (a "collection window") that is a fixed period of time, includes a finger warmer, and includes an integrated finger-lancing element.

In embodiments, a system having features as disclosed herein is configured to provide automated finger-pressure cycling and to indicate a collection period (a "collection window") that is a fixed period of time. In embodiments, a system having features as disclosed herein is configured to provide automated finger-pressure cycling, to indicate a collection period (a "collection window") that is a fixed period of time, and includes a finger warmer. In embodiments, a system having features as disclosed herein is configured to provide automated finger-pressure cycling, to indicate a collection period (a "collection window") that is a fixed period of time, includes a finger warmer, and includes an integrated finger-lancing element.

Figure 5:
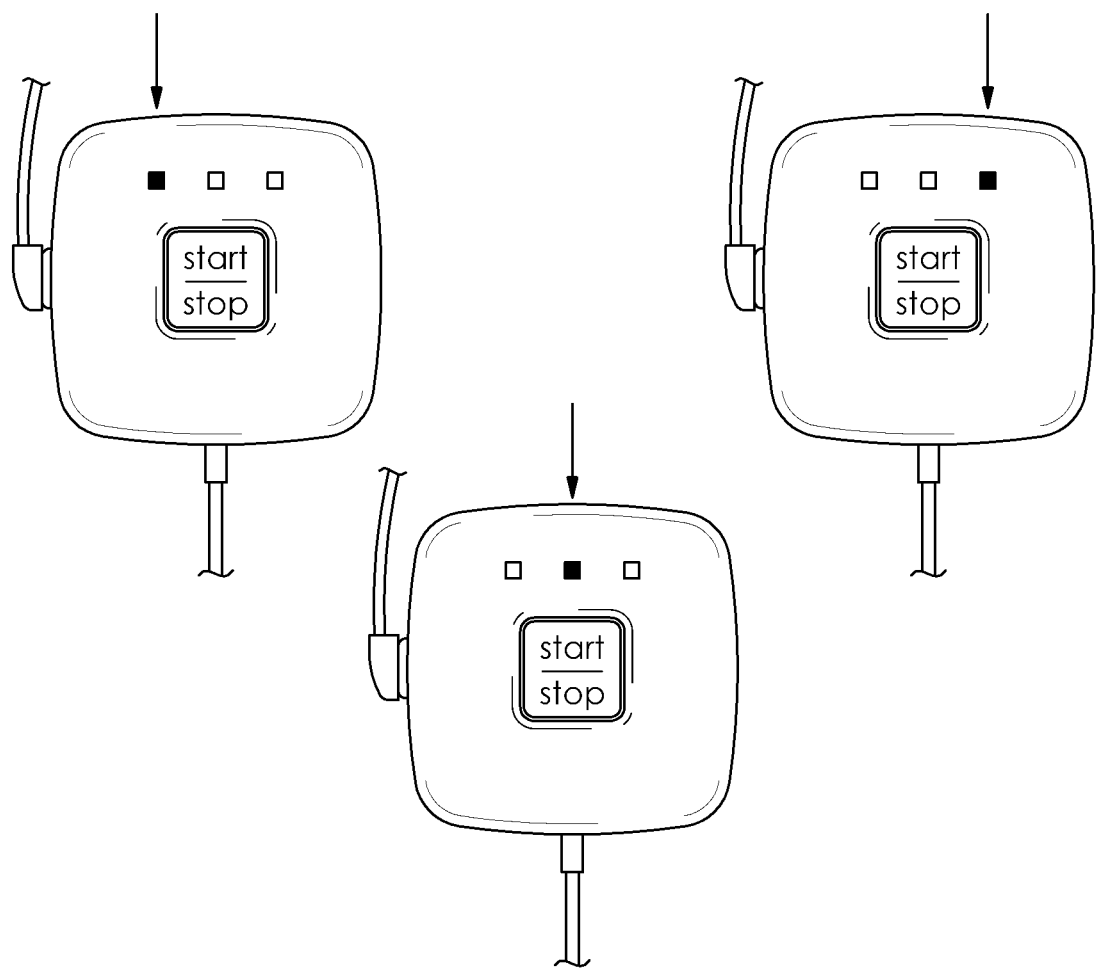
FIG. 5 shows housings and portions of a conduit and a power connection of devices having features as disclosed herein, providing examples of devices in three possible configurations. Individual configurations are indicated by illumination of indicator lights. The left-most indicator light of the device depicted on the left of the figure is shown illuminated to indicate that pressure is being applied by the device to a finger of a subject. The central indicator light of the device depicted in the middle of the figure is shown illuminated to indicate that a lancet is to be applied to a finger of a subject to provide a fingerstick wound for obtaining blood from the subject. The right-most indicator light of the device depicted on the right of the figure is shown illuminated to indicate that blood may be collected from the fingerstick wound of the finger of the subject.

FIG. 5 shows housings and portions of conduits and power connections of devices having features as disclosed herein, providing examples of indicator lights in different configurations. Individual configurations are indicated by illumination of indicator lights. The left-most indicator light of the device depicted on the left of the figure is shown illuminated to indicate that pressure is being applied by the device to a finger of a subject. The central indicator light of the device depicted in the middle of the figure is shown illuminated to indicate that a lancet is to be applied to a finger of a subject to provide a fingerstick wound for obtaining blood from the subject. The right-most indicator light of the device depicted on the right of the figure is shown illuminated to indicate that blood may be collected from the fingerstick wound of the finger of the subject.

Figure 6:
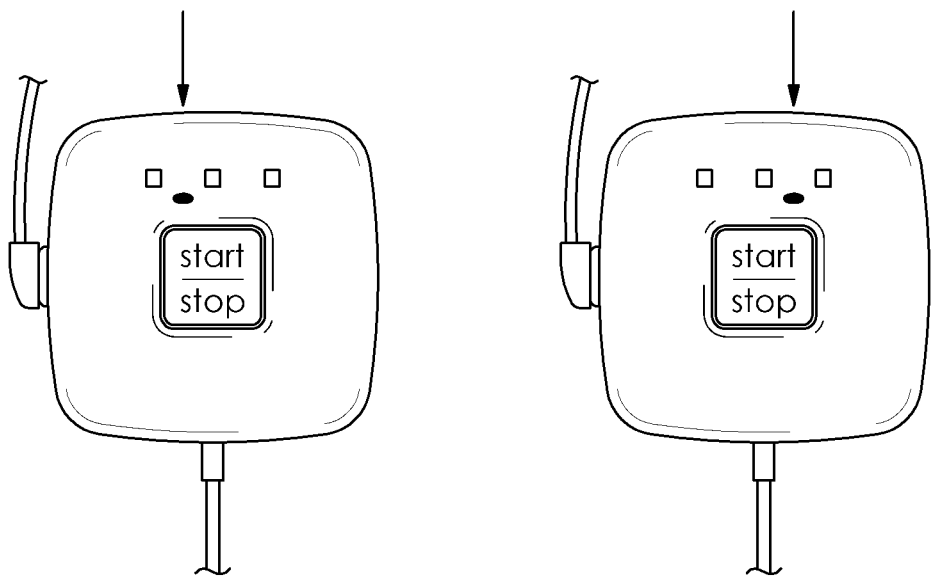
FIG. 6 shows housings and portions of conduits and power connections of devices having features as disclosed herein, providing examples of devices with error indicator lights lit in each of two configurations. Individual configurations are indicated by illumination of indicator lights. The left error indicator light of the device depicted on the device on the left portion of the figure is shown illuminated to indicate that an error condition has occurred related to the pressure cuff. The right error indicator light of the device depicted on the right portion of the figure is shown illuminated to indicate that an error condition has occurred related to the foot pedal (which is used to interrupt the sequence of pressure pulses in the cuff).

FIG. 6 shows housings and portions of conduits and power connections devices having features as disclosed herein. The figures show indicator lights for alerting a user of the occurrence of an error. FIG. 6 shows indicator lights lit in each of two configurations. Individual configurations are indicated by illumination of indicator lights. The left error indicator light of the device depicted on the device on the left portion of the figure is shown illuminated to indicate that an error condition has occurred related to the pressure cuff. The right error indicator light of the device depicted on the right portion of the figure is shown illuminated to indicate that an error condition has occurred related to the foot pedal (which is used to interrupt the sequence of pressure pulses in the cuff).

Figure 7A:
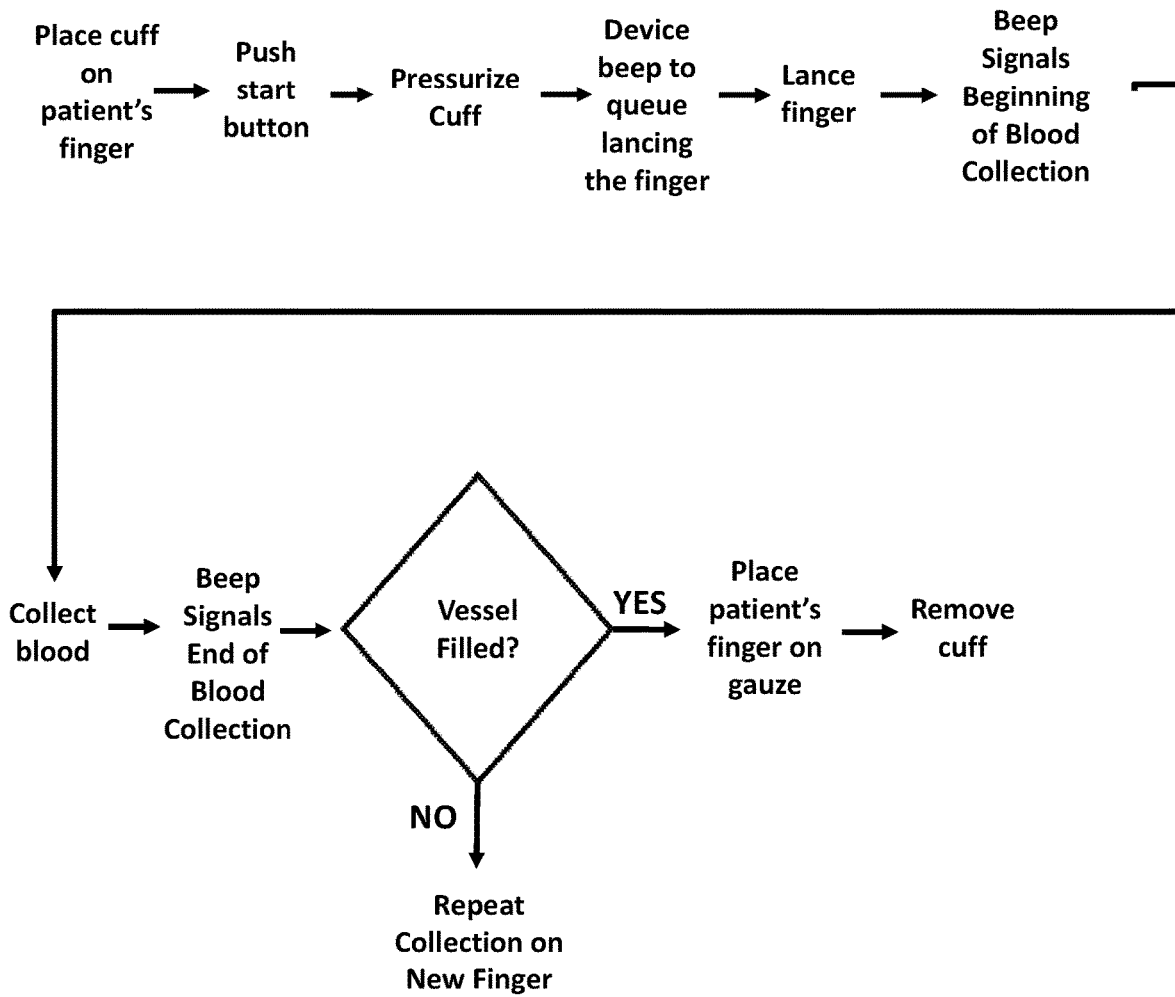
FIG. 7A provides a schematic diagram detailing steps of obtaining a fingerstick blood sample according to methods of using the devices and systems disclosed herein. The figure explicitly names the digit as a finger, although a fingerstick blood sample may be obtained from a toe, or other body surface.

FIG. 7A provides a schematic diagram detailing steps for obtaining a fingerstick blood sample according to methods of using the devices and systems disclosed herein. The figure explicitly names the digit as a finger, although a fingerstick blood sample may be obtained from a toe, or other body surface. As illustrated in FIG. 7A, a cuff is placed on a digit (e.g., a finger), and the start button is pressed, initiating inflation of the cuff. Inflation of the cuff constricts the digit and occludes blood flow in the digit, preparing it for collection of a fingerstick blood sample. Proper placement of the cuff leaves at least about 5 mm of skin surface of the digit exposed following inflation of the cuff; for example, at least about 5 mm of the distal (tip) portion of a digit such as a finger or toe may be left exposed while the cuff is in place and is inflated. A cuff of the devices and systems disclosed herein is sized so as to provide sufficient exposed skin surface when inflated and disposed in place on a digit. A signal (e.g., an audible signal, such as a beep, as indicated in FIG. 7A) is provided by the device to alert a user that constriction by the cuff has proceeded for a sufficient amount of time, and that the digit may be lanced. The digit is lanced, and a further signal indicates that collection of blood may proceed. Blood is collected from the wound site, and, a further alert (e.g., a further audible signal) is provided at the end of the period of time during which a high quality fingerstick blood sample may be collected. The alert signals the end of the collection period. Blood collection ends at this time (if blood collection was still proceeding; in many cases, sufficient amount of blood is collected prior to reaching the end of the collection period).

If a sufficient amount of blood was collected by, or prior to, the end of the collection period (as indicated by the question "Vessel Filled?" in FIG. 7A), the sample is placed in a storage container or location, or is placed in a transport container, or is provided to a sample analysis device or system for analysis. Gauze, bandage, or other treatment may be placed on, or applied to, the digit. The cuff is deflated, and may be removed from the digit.

If, however, an insufficient amount of blood was collected by, or prior to, the end of the collection period, a further sample, typically obtained from a different digit, may be obtained, by beginning the steps again from the beginning. If a portion of the desired amount is still of use, then that portion may be placed in a storage container or location, or is placed in a transport container, or is provided to a sample analysis device or system for analysis. If a too-small amount of blood makes the desired analysis impossible, then the sample may be discarded.

Figure 7B:
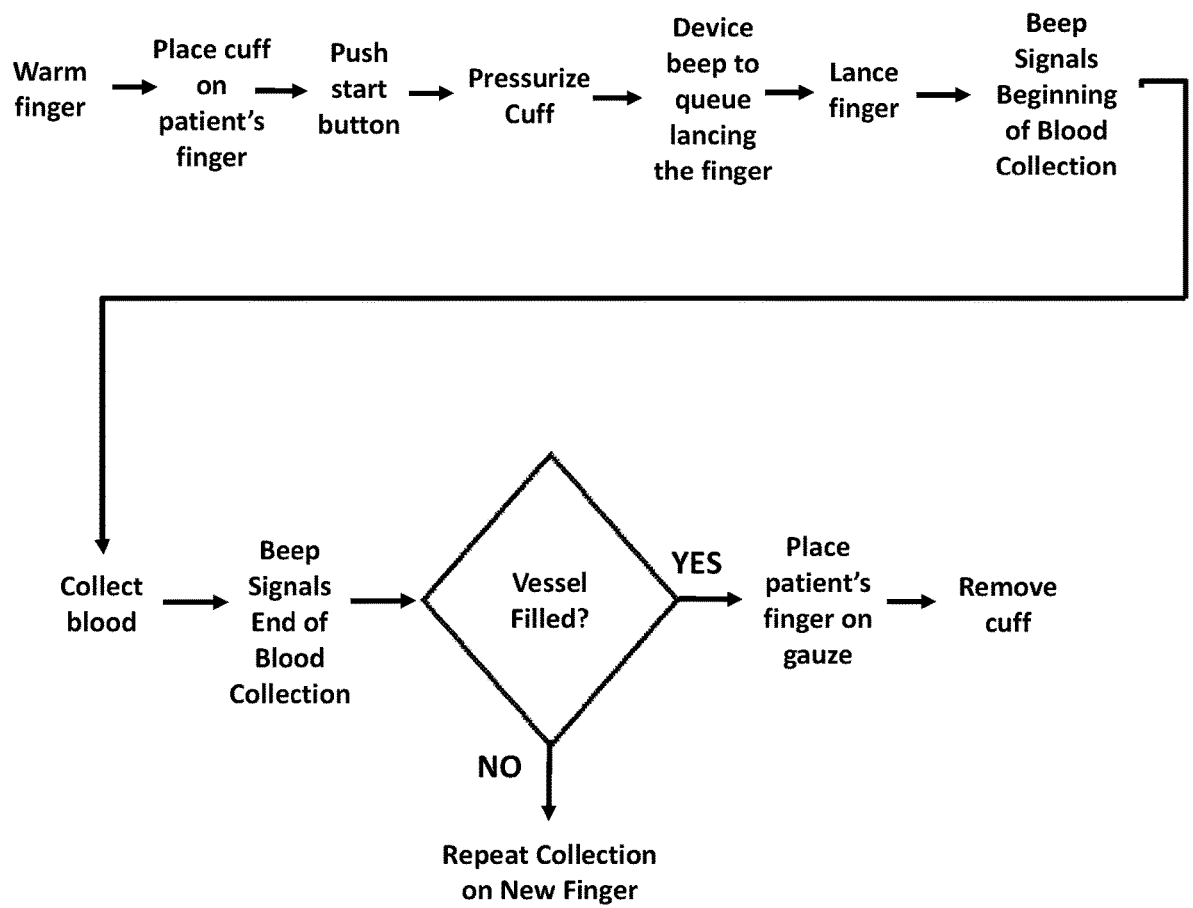
FIG. 7B provides a schematic diagram detailing steps of obtaining a fingerstick blood sample according to methods of using the devices and systems disclosed herein, in which a digit (e.g., a finger) is warmed prior to placing a cuff on the digit.

FIG. 7B provides a schematic diagram detailing steps of obtaining a fingerstick blood sample according to methods of using the devices and systems disclosed herein, in which a digit (e.g., a finger) is warmed prior to placing a cuff on the digit. These steps are identical to those shown in FIG. 7A, with the difference that the steps of FIG. 7B further include a step of warming the digit prior to beginning fingerstick blood collection. A digit may be warmed for at least about 45 seconds prior to sample collection, and may be warmed for about 50 seconds, or about 60 seconds, or about 70 seconds, or about 80 seconds, or more. Warming a digit prior to sample collection may begin prior to placement of the cuff on the finger (e.g., as shown in FIG. 7B), or may begin with placement of the cuff on the digit, or may begin following placement of the cuff on the digit. Warming typically begins prior to inflation of the cuff on the digit. As indicated, for example, in FIG. 2B, a cuff may include a warming mechanism, which may be activated effective to warm a digit when the cuff is placed on the digit. In embodiments, a warming mechanism may be separate from a cuff; such a warming mechanism may be applied prior to, or during, placement of the cuff on the digit, or while the cuff is in place on the digit. In embodiments, a separate warming mechanism may be applied to a digit and a warming mechanism in a cuff may be activated (e.g., while the cuff is in place on the digit). In embodiments, a separate warming mechanism may be applied to a digit prior to placement of a cuff on the digit, and a warming mechanism in a cuff may be activated after the cuff is in place on the digit.

An interrupt switch 36 may be configured to be operated with minimal interference with collection of a fingerstick blood sample; for example an interrupt switch 36 may be a foot pedal, which a technician may operate at the same time that technician is collecting blood from a subject without requiring the use of a hand to interrupt pressure application. An interrupt switch 36 configured to interrupt pressure application is optional; some embodiments of the devices disclosed herein may lack an interrupt switch 36.

As discussed above, an interrupt switch (e.g., an interrupt switch 36 as shown in FIGS. 2A-2E and in 3A and 3B) may interrupt pressure application, or allow pressure release, or both, effective to interrupt the inflation of a cuff while the interrupt switch is activated. In embodiments, activation of an interrupt switch pauses the pressure cycling of the cuff to allow blood flow rate control. In embodiments, an interrupt switch may be a foot pedal, and pressing the foot pedal may pause the pressure cycling of the cuff to allow blood flow rate control. Activation of an interrupt switch provides a temporary pause in inflation of a cuff; typically, where a sample collection vessel is filled before the end of the full time period for collection of a fingerstick blood sample, the "stop" button may be pressed to end the collection program.

The devices and systems disclosed herein may be operated by a technician for use on a patient to collect a sample of blood from the patient. In embodiments, use of the devices and systems disclosed herein for obtaining a blood sample from a patient are simple to use, and, in use, cause only minimal discomfort to a patient. In embodiments, a technician (user) may easily and readily use the devices and systems disclosed herein with minimal training. Some types of users of the devices and systems disclosed herein are discussed in the following.

In embodiments, users of devices and systems disclosed herein will be trained on the device use prior to operating the product. Users of the devices and systems disclosed herein include phlebotomists, technicians, and trainers. Phlebotomists may be certified by an appropriate certification entity.

Trainers: Trainers are personnel who are thoroughly trained and educated on the Fingerstick Blood Collection Process. Trainers are capable of training Technicians and Phlebotomists in the field. Trainers will typically have a minimum of a college degree, which need not be in a technical field.

Phlebotomists: Phlebotomists will typically have training and experience with fingerstick and/or heel stick blood collection methods. In most cases, however, the primary focus of phlebotomy training programs is venous-based blood collection, so that phlebotomists may benefit from focused training, such as may be available from trainers. Certified phlebotomists are required to have a minimum of a high school diploma as a prerequisite to any phlebotomy certification program.

Technicians: Technicians may have little or no prior experience with any type of blood collection or patient interaction, and may not necessarily have a high school diploma. Technicians should receive training on fingerstick blood collection methods and techniques prior to using the devices and systems, and prior to practicing the methods, disclosed herein.

In embodiments, only a minimal amount of training is required to train a technician in the operation and use of a device or system for automatically providing cycling pressure application to a digit of a subject. In embodiments, a minimal amount of training is only about 30 minutes of training, or may be less than about 30 minutes of training, in order that a technician receive sufficient training to be able to properly and safely operate the devices and systems, and to properly and safely collect fingerstick samples from subjects.

Devices and systems disclosed herein are designed to directly replace manual pressure cycling of the patient's finger during fingerstick blood collection. Thus, use of the methods, devices, systems, and kits disclosed herein will obviate any need to manually manipulate a subject's extremity during fingerstick blood collection.

In embodiments, devices and systems disclosed herein will typically be operated in indoor environments where electricity is available. In embodiments, devices and systems disclosed herein may be used on adult subjects, and in embodiments, may be used on pediatric subjects, such as children and infants.

In embodiments, the devices for automatically providing cycling pressure application to a digit of a subject are table-top devices (i.e., devices of small enough size to fit on a normal table during use). In embodiments, systems including a device for automatically providing cycling pressure application to a digit of a subject are table top systems. In embodiments, a table-top device or system will have a housing with a largest dimension that is smaller than about three feet, or is smaller than about two feet, or is smaller than about 1 foot in size. In embodiments, a table-top device or system will have a housing that weighs less than about 30 pounds, or less than about 20 pounds, or less than about 10 pounds.

In embodiments, the devices for automatically providing cycling pressure application to a digit of a subject integrate into the existing environment and workflow of a clinical laboratory, physician's office, retail location, or other location where fingerstick samples may be collected. In embodiments, systems including a device for automatically providing cycling pressure application to a digit of a subject integrate into the existing environment and workflow of a clinical laboratory, physician's office, retail location, or other location where fingerstick samples may be collected.

Kits

In embodiments, kits for collecting blood from a digit are disclosed herein. In embodiments, kits for collecting blood from a digit include a device as disclosed herein, and a sample collection vessel. In embodiments, kits for collecting blood from a digit comprise a device as disclosed herein, a sample collection vessel, and a disposable for use in sample collection. In embodiments, kits for collecting blood from a digit comprise a device as disclosed herein, a sample collection vessel, a lancet for puncturing a digit, and a disposable for use in sample collection. In embodiments, kits for collecting blood from a digit comprise a disposable selected from the group of disposables consisting of a swab, a sterile swab, an absorbent pad, and a bandage.

Applicant discloses herein kits including devices or systems as disclosed herein, and further including a sample collection device or sample collection vessel suitable for collecting a fingerstick blood sample. Applicant discloses herein kits including devices or systems as disclosed herein, and further including a sample transport vessel suitable for transporting a fingerstick blood sample from a site of collection to another location (e.g., to a laboratory location). Sample collection devices and vessels are disclosed, for example, in U.S. patent application Ser. No. 14/020,435, filed Sep. 6, 2013; U.S. patent application Ser. No. 14/098, 177, filed Dec. 5, 2013; U.S. patent application Ser. No. 14/214,774, filed Mar. 15, 2014; U.S. patent application Ser. No. 14/320,471, filed Jun. 30, 2014; U.S. patent application Ser No. 14/446,080, filed Jul. 29, 2014; and U.S. patent application Ser. No. 14/447,099, filed Jul. 30, 2014, the entire contents of which patent applications are hereby incorporated by reference in their entireties for all purposes.

Kits disclosed herein may include devices or systems as disclosed herein, and further include a disposable useful in or after collecting a fingerstick blood sample; for example a disposable may be a lancet (which may be, e.g., a blade or a needle), such as a manually operated lancet, a spring-operated lancet, a lancet having a sheath, or other lancet. Kits disclosed herein may include devices or systems as disclosed herein, and further include a disposable for use in collecting a fingerstick blood sample, where, for example the disposable is a bandage, a gauze pad, an absorbent pad, a swab, a sterile swab, or other disposable. Kits disclosed herein may include devices or systems as disclosed herein, and further include a disposable for use in collecting a fingerstick blood sample, where, for example the disposable is a label, such as, e.g., a bar-code label, or a QR code label, or other label.

Uses

The methods, devices, and systems disclosed herein may be used to obtain blood samples from subjects, including adult (standard cuff), pediatric (smaller cuff), geriatric (typically standard cuff), and other subjects. Blood samples may be obtained from a digit of a subject, e.g., from a finger or fingers of a subject. In embodiments, blood samples may be obtained from a toe or toes of a subject. The methods, devices, and systems disclosed herein may be used to obtain blood samples for clinical use, e.g., for clinical diagnostic use. Clinical uses may include routine clinical testing, esoteric clinical testing, screening for the presence of drugs or drug metabolites; screening for the presence or absence of disease markers; screening for the presence or absence of genetic markers; paternity testing; determination of ancestry; and for other reasons and purposes.

In embodiments, the methods, devices, and systems disclosed herein may be used to obtain blood samples for research use. In embodiments, the methods, devices, and systems disclosed herein may be used to obtain blood samples for use by insurance companies in determining the suitability of insurance coverage, or the cost of insurance coverage, for a subject; for identification of a subject; for administrative purposes; for archival purposes; and for any other purpose for which a blood sample may be obtained.

Devices for collecting blood from a digit as disclosed herein may be located any suitable location. In embodiments, such a suitable location may include a clinical laboratory, a hospital, a doctor's office, a clinic, a retail store, a school, a community center, a library, and combinations thereof. In embodiments, devices for collecting blood from a digit as disclosed herein are located at a point-of-care location. In embodiments, such a point-of-care location is selected from the group of point-of-care locations consisting of a hospital, a doctor's office, a clinic, and combinations thereof.

Systems for collecting blood from a digit as disclosed herein may be located any suitable location. In embodiments, such a suitable location may include a clinical laboratory, a hospital, a doctor's office, a clinic, a retail store, a school, a community center, a library, and combinations thereof. In embodiments, devices for collecting blood from a digit as disclosed herein are located at a point-of-care location. In embodiments, such a point-of-care location is selected from the group of point-of-care locations consisting of a hospital, a doctor's office, a clinic, and combinations thereof.

EXAMPLES

Exemplary methods for using the devices and systems disclosed herein are discussed in the following. In the following, reference is made to the device; it will be understood that such references apply with equal force to systems as disclosed herein, which systems include such devices. The user of the devices and systems disclosed herein is termed a "technician" in the following examples; it will be understood that this technician may be any user capable of operating the devices and systems during fingerstick blood sample collection as disclosed herein. In the following examples, the digit from which a fingerstick blood sample is collected is termed a "finger"; however, it will be understood that any digit, including a toe, or other skin surface (e.g., a heel, or earlobe) may be used to collect a fingerstick blood sample. In the following, the subject from whom the fingerstick blood sample is collected is identified as the "patient"; however, it will be understood that any person, whether a patient suffering from a disease, or being monitored for a medical condition, or undergoing for routine medical testing, or a research subject, or other subject, may be the source of a fingerstick blood sample.

Performance Features and Characteristics for Normal Operation

Devices and systems for collection of fingerstick blood samples are disclosed herein. Devices having features as disclosed herein may be used in, and make up part of, systems having features as disclosed herein. Methods for the use of these devices and systems for collecting fingerstick blood samples are disclosed herein. Operation of these devices and systems may be performed according to such methods; in embodiments, operation of these devices and systems may be according to a program. Such a program may include automatic steps, including a pre-determined order of steps, which govern the operation of a device or system as disclosed herein. In embodiments, as used in the following, the term "the program" refers to a process that includes many or all steps for collection of a fingerstick blood sample using a device or using a system disclosed herein. Devices may include a processor, and may include memory (e.g., digital memory, such as read-only memory, random access memory, flash memory, or other memory, or combinations thereof). Such memory may be effective to store a program for operation of a device as disclosed herein. A processor, or a processor and memory, may be effective to control the operation of a device as disclosed herein. Devices and systems may further include a timing mechanism (e.g., a timer such as a timing chip, a mechanical timer, or other timer), which may be operably configured for use with a processor, or for use with a processor and memory, effective to control the operation of a device as disclosed herein according to times and time periods as needed for the operation of a device for collecting fingerstick blood samples.

In embodiments, devices as disclosed herein may include a housing. In embodiments, such a housing may enclose a processor. In embodiments, such a housing may enclose digital memory, or other form of electronic memory. In embodiments, such a housing may enclose a timing mechanism. In embodiments, such a housing may enclose a pressure source. In embodiments, such a housing may enclose a power supply, or a battery, or other elements for providing power to other components of the device or for converting power to a suitable form or use by other components of the device. A housing may have a switch, such as an ON/OFF switch, and may have a plurality of switches, each of which may be accessible for use by a user of the device. A housing may have an indicator, such as an indicator light, visible to a user of the device, or otherwise capable of providing an indication to a user of the device. A housing may have a plurality of indicators. A housing may have a sound generator, such as a beeper, speaker, or bell, and may have a plurality of sound generators, each of which may be audible by a user of the device when activated. A housing may have a connector configured to receive and hold a conduit; in embodiments, such a connector may be configured to provide pressure from a pressure source to a conduit. In embodiments, such a conduit may include a cuff, or may be configured to accept or carry a cuff, where the cuff is an inflatable cuff configured for placement on a digit.

Devices having features as disclosed herein may be designed and configured to provide the following outputs and performance characteristics.

These devices may be configured to apply pressure to the circumference of the patient's finger at a repeatable distance from the fingertip. In embodiments, such a distance is about 5 to 25 mm from the tip (or other extreme portion of the digit). In embodiments, such a distance is about 5 to 10 mm from the tip (or other extreme portion of the digit). In embodiments, such a distance is at least about 5 mm from the tip (or other extreme portion of the digit).

These devices may be configured to use audio cues to provide feedback to the user. In this way, the user (operator) is able to remain focused on the patient and on the task of blood collection into the device or into a sample collection vessel. Such device audio cues may be provided at one or more of: at the start of the program, the start of the lancing period, the start of the collection period, the end of the program, and for all errors. These devices may be configured to indicate program progress and error status to the user. These devices may have a single button to start and stop the device program.

These devices may have a foot pedal which deflates the cuff while the pedal is pushed. Pressing the foot pedal does not impact the program timer. Use of the foot pedal allows the user to control the flow rate of blood from the finger by allowing the user to briefly interrupt cuff inflation and allow a period of cuff deflation. These devices may be configured to provide a tourniquet period during which the cuff is inflated for 3 seconds. Such a tourniquet period mimics manual collection technique (i.e., techniques in which a technician manually squeezes a digit in order to constrict the digit and reduce or prevent blood flow out of the digit). Applying a tourniquet-like grip on the finger is thought to help to reduce the pain associated with lancing and to help collect the blood into the finger. These devices may be configured to have a lancing period during which the cuff remains inflated for 5 seconds after the lancing audio cue. This mimics manual collection technique. These devices may be configured to have a collection period during which the cuff is cyclically held inflated for 1 second then deflated for 1 second for a total of 60 seconds after the lancing cue. In one non-limiting example, the collection window is a 60 second collection window based on studies indicating that after 60 seconds, the likelihood of collecting clotted blood samples is increased for some patients. In embodiments, the collection window may be a 70 second collection window, or may be a 80 second collection window. These devices may be configured to be capable of detecting pressure problems with the cuff and of indicating an error. These devices may be configured to be capable of detecting whether the foot pedal is plugged in and indicate an error if it is missing. These devices may be configured to deflate the cuff and discontinue operation if an error state is detected. Optionally, some embodiments may adjust the length of the collection window based on exogenous factors such as but not limited to the time of the year (e.g., winter, summer, fall, or spring), current temperature, barometric pressure, or other factor(s) that may impact the sample collection process. This information may be communicated to the pressure application device or the device may have sensors to measure such exogenous factors directly.

In embodiments, use of these devices may allow collection of a 200 fingerstick blood sample volume within a sample collection period of about 90 seconds. In embodiments, use of these devices may allow collection of a 200 µL fingerstick blood sample volume within a sample collection period of about 80 seconds. In embodiments, use of these devices may allow collection of a 200 µL fingerstick blood sample volume within a sample collection period of about 70 seconds. In embodiments, use of these devices may allow collection of a 200 µL fingerstick blood sample volume within a sample collection period of about 60 seconds.

These devices may be configured to inflate a cuff to a pressure of about 300 mm Hg during normal operation; in embodiments, a cuff may be inflated to a pressure of about 300 mm Hg in less than 10 seconds, or in less than 5 seconds, in less than 3 seconds, in less than 2 seconds, in less than 1 seconds. These devices may be configured to maintain the cuff inflation pressure of about 300 mmHg over a period of 10 seconds. These devices may be configured to prevent inflation of the cuff over a pressure of 300 mm Hg. In embodiments, these devices may be configured to deflate a cuff in less than 3 seconds after the stop button is pressed, in less than 2 seconds after the stop button is pressed, or in less than 1 second after the stop button is pressed.

In embodiments, a cuff of a device having features as disclosed herein may be disposable; use of disposable cuffs may reduce or prevent patient-to-patient contamination. In embodiments, these devices, including cuffs of these devices, may be made of materials suitable for cleaning; for example, these devices may be made of materials suitable for wiping by isopropyl alcohol-based disinfectant wipes or by other disinfectant wipes.

These devices may be configured for use with subjects having digits of a wide range of digit size. In embodiments, devices having features as disclosed herein may be configured to operate with digits ranging in size from as small as the size of a finger of the smallest $1^{st}$ percentile of adult females up to as large as the size of a finger of the largest $99^{th}$ percentile adult males. For example, cuffs having features as disclosed herein may be configured to operate with digits ranging in size from about 1 centimeter (cm) to about 3 cm in diameter. In embodiments, cuffs having features as disclosed herein may be configured to operate with digits ranging in size from about 1.3 cm to about 2.5 cm diameter.

In embodiments of devices having features as disclosed herein, cuffs may be sized so as to allow a gap of about 5 mm or more as measured from the patient's fingertip to the cuff to allow space for lancing the finger. In embodiments, such a gap may be a gap of about 10 mm or more. In embodiments of methods using devices having features as disclosed herein, cuffs may be placed on a digit so as to allow a gap of about 5 mm or more as measured from the patient's fingertip to the cuff to allow space for lancing the finger. In embodiments, cuffs may be placed on a digit so as to allow a gap of about 10 mm or more. These devices may be capable of operating on the patient's left hand (or foot) or on the patient's right hand (or foot). These devices may be configured for operation by a left-handed or by a right-handed technician. These devices may be configured for operation by a technician wearing gloves. In embodiments, these devices may be configured for use with electrical power that is typically available from standard wall-sockets. In embodiments, these devices may be battery powered. In embodiments, these devices may be powered by rechargeable batteries. In embodiments, these devices may be configured for use with either batteries or with electrical power that is typically available from standard wall-sockets. Devices having features as disclosed herein are typically simple to setup and simple to operate; in embodiments, these devices may be capable of operation within less than about 10 minutes of the initial installation of the device.

Normal Use Case: Collection Completed Prior to Collection Window Expiration

In normal use in collecting a fingerstick blood sample from a subject, the following steps are taken. 1) Technician attaches a new cuff to the device. In embodiments, the conduit providing pressure from the housing of the device (in which the pressure source may be located) to the cuff is part of the device, and is configured to mate with a disposable cuff. In embodiments, the cuff is permanently attached to the conduit providing pressure from the housing of the device, so that the cuff and the conduit form a single unit which may be attached to the housing in which the pressure source may be located. 2) Technician places the cuff on the patient's finger and slides it back toward the palm as far as possible to allow space for disinfecting the finger. 3) Technician disinfects the patient's finger with an alcohol wipe and allows it to dry. 4) Technician places cuff at the indicated distance from the patient's fingertip and supports the finger with his/her non-dominant hand. 5) Technician hits a start button on the device and picks up the lancet with his/her dominant hand. 6) The device beeps and pressurizes the cuff to tourniquet the patient's finger for 3 seconds. 7) The device beeps to indicate to the Technician to lance the finger and holds pressure for 5 seconds during the lancing period. 8) The Technician lances the patient's finger, places the lancet in a sharps container, and picks up the blood collection device and begins collecting the blood. 9) The device beeps to indicate the start of the collection period and begins to cycle squeezing and releasing pressure on the patient's finger. 10) The Technician collects the blood produced into the collection device until the device is full. 11) The Technician hits the pause pedal to stop the pressurizing the finger, places the patient's finger on the gauze, and asks the patient to apply pressure to stop any bleeding. 12) The Technician operates the blood collection device, and then presses the stop button on the device to end the program (if the collection window has not expired). The collection window is typically 60 seconds, and (optionally) may be 70 seconds or 80 seconds. 13) The technician removes the cuff from the patient's finger then places a bandage on the finger. 14) The cuff may be detached from the housing of the device and disposed in the trash. In embodiments, the conduit connecting the cuff to the housing (which contains the source of pressure) may be re-used by attaching a new cuff to the conduit for use with a subsequent subject. In embodiments, the conduit and the cuff may be provided as a single unit, and that unit (including the conduit and the cuff) may be detached from the housing and discarded, and a new conduit and the cuff unit attached to the housing for use with a subsequent subject. Optionally, some embodiments may have a cuff unit or other pressure application unit that has a tear-away contact layer that covers any portion of the cuff unit or pressure application unit that may be pressing against the subject. In such a non-limiting embodiment, the tear-way portion can be replaced each time a new patient or subject is being processed without having to completely replace the cuff unit or pressure application unit for each collection event. This may reduce costs in terms of minimizing the amount of equipment to replace for each collection event. In one non-limiting example, the tear-away portion may use an adhesive, VELCRO™ connectors, hook/loop/fabric connectors, or other releasable connections for attaching a tear-away sheet, membrane, or other covering for disposal after each use. Some embodiments may incorporate a heating element, chemical heat-pad, or the like with the disposable cover or layer portion.

Alternative Use Case: Patient Blood Flow Rate too High for Collection Device

If, in step 8 or 10 above, the blood flow from the fingerstick wound is too high to collect into the blood collection device, then the following methods may be performed.

1) The technician press and holds the pause (foot) pedal which causes the device to depressurize the finger until the pedal is released. This allows the technician to control the blood flow rate from the finger. Note: pressing the pause pedal does not affect the collection timer; the collection window remains fixed.

2) Release of the pause pedal causes the device to continue pressurizing the finger.

Alternative Use Case: Foot Pedal Not Attached.

If in step 5 of the Normal Use Case, the device does not detect that the foot pedal is connected: 1) The device will show a foot pedal error and not start the collection program. 2) The technician plugs in the foot pedal and the error resets. 3) The technician continues with step 5 of the Normal Use Case.

Alternative Use Case: Cuff Not to Pressure

If during step 6, the device does not reach the pressure set point, then: 1) The device will show a cuff error and discontinue the collection program. 2) The technician will check the cuff for possible causes of the error (e.g., cuff not attached; cuff leaking; cuff not properly affixed around finger; or other cause). 3) The technician continues with step 5 of the Normal Use Case.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. By way of non-limiting example, although many embodiments herein describe the use of a pneumatic system for application of pressure, it should be understood that other techniques for application of pressure such as but not limited to mechanical, electromechanical, piezoelectric, or other current technologies or those to be developed in the future may be used to apply a desired amount of pressure to a portion of the subject. Some embodiments may use at least one of linear actuators, pistons, screw-drives, worm-drives, pneumatic actuators, voice coil-type actuators, diaphragms, or other devices to provide the desired pressure. Some embodiments may use single or multiple combinations of the foregoing to provide a desired pressure or pattern of applied pressure. Some embodiments may be configured to apply pressure to more than one digit on the same hand. Some embodiments may be configured to apply pressure to at least one digit on a first body party and a least another digit on a second body part. In some embodiments, a warming pad or other warming component may be part of the device in contact with the subject and may be detached, moved, or otherwise positioned to reveal a target site for sample collection after the target site has been sufficiently warmed, wherein such uncovering or unveiling of the target site does not impact the pressure application portions of the device. Optionally, some embodiments may use a non-contact warming technique such as but not limited to an infrared heating, laser, or other non-direct contact heating technique.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, and so forth.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for".

We claim:

1. A method for collecting blood from a human digit comprising:
at least partially encircling the human digit with a cuff;

inflating the cuff using a device having a pressure source and a pressure-interruption switch, the device effective to apply pressure to the digit;

lancing the digit effective to puncture a skin of the digit and to allow blood to flow out of the digit; and collecting of at least a portion of the blood flowing out of the digit;

controlling the pressure source and pressure-interruption switch with a control unit in the device to provide a plurality of cuff inflations and cuff deflations at a desired frequency between a beginning and an end of a period of time.

2. The method of claim 1, wherein the collecting of the at least the portion the blood comprises collecting the blood flowing out of the digit for about 60 seconds following the lancing of the digit.

3. The method of claim 1, wherein the collecting of the at least the portion of the blood comprises deflating the cuff.

4. The method of claim 1, wherein the inflating the cuff comprises inflating the cuff to a maximum pressure of about 300 millimeters (mm) of mercury (Hg) of pressure.

5. The method of claim 1, wherein the collecting of the at least the portion of the blood flowing out of the digit comprises beginning the collection of the blood flowing out of the digit pursuant to a signal from the device.

6. The method of claim 5, wherein the signal includes at least one of an audible signal, a visual signal, or a tactile signal.

7. The method of claim 1, further comprising ending the collection of the blood flowing out of the digit pursuant to a signal from the device.

8. The method of claim 1, wherein the collecting of the at least the portion of the blood flowing out of the digit comprises:

beginning the collection of the at least the portion of the blood flowing out of the digit pursuant to a first signal from the device; and ending the collection of the blood flowing out of the digit pursuant to a second signal from the device.

9. The method of claim 8, wherein each of the first signal and the second signal includes at least one of an audible signal, a visual signal, or a tactile signal.

10. The method of claim 1, wherein the device further comprises a timer configured to determine said period of time, wherein the period of time is a desired period of time for collecting a fingerstick blood sample from the digit.

11. The method of claim 1, further comprising providing a signal at the end of the period of time.

12. The method of claim 1, further comprising providing a signal at the beginning of the period of time.

13. The method of claim 1, further comprising ending the inflation of the cuff at the end of the period of time.

14. The method of claim 1, further comprising sending an electronic, hydraulic, or mechanical signal to a sample collector to end the collection of the blood flowing out of the digit.

15. The method of claim 1, wherein inflating the cuff comprises inflating the cuff followed by at least partially deflating the cuff.

16. The method of claim 15, wherein the plurality of cuff inflations and cuff deflations at a desired frequency comprises pulsing at a pulse frequency of at least about 15 cycles per minute, where a cycle consists of an inflation and a deflation of the cuff.

17. The method of claim 15, wherein the plurality of cuff inflations and cuff deflations at a desired frequency comprises pulsing at a pulse frequency of at least about 20 cycles per minute, where a cycle consists of an inflation and a deflation of the cuff.

18. The method of claim 1, wherein the cuff further comprises a warmer configured to warm the digit disposed within the cuff, and the warming of the digit is effected at least in part by the warmer.

19. The method of claim 18, wherein the warming of the digit includes warming the digit for a warming period of at least 45 seconds.

* * * * *